(12) United States Patent
Dobrinsky et al.

(10) Patent No.: US 10,517,974 B2
(45) Date of Patent: Dec. 31, 2019

(54) ULTRAVIOLET SURFACE ILLUMINATION SYSTEM

(71) Applicant: Sensor Electronic Technology, Inc., Columbia, SC (US)

(72) Inventors: Alexander Dobrinsky, Loudonville, NY (US); Michael Shur, Latham, NY (US); Emmanuel Lakios, Mount Sinai, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 189 days.

(21) Appl. No.: 15/478,759

(22) Filed: Apr. 4, 2017

(65) Prior Publication Data

US 2017/0290934 A1 Oct. 12, 2017

Related U.S. Application Data

(60) Provisional application No. 62/356,696, filed on Jun. 30, 2016, provisional application No. 62/330,368, (Continued)

(51) Int. Cl.
*A61L 2/10* (2006.01)
*G02B 3/08* (2006.01)
(Continued)

(52) U.S. Cl.
CPC .................. *A61L 2/10* (2013.01); *G02B 3/08* (2013.01); *G02B 5/0284* (2013.01);
(Continued)

(58) Field of Classification Search
CPC ........... A61L 2/10; A61L 2/0047; G02B 3/08; G02B 5/0284; G02B 5/0891; G02B 5/10; G02B 6/001; G02B 6/02
See application file for complete search history.

(56) References Cited

U.S. PATENT DOCUMENTS 7,553,456 B2    6/2009   Gaska et al.
7,634,996 B2   12/2009   Gaska et al.
(Continued)

FOREIGN PATENT DOCUMENTS

KR   10-2012-0105810 A    9/2012
WO        2015035132 A1    3/2015

OTHER PUBLICATIONS

International Application No. PCT/KR2017/003809, International Search Report and Written Opinion, dated Jul. 10, 2017, 11 pages.

*Primary Examiner* — Wyatt A Stoffa
(74) *Attorney, Agent, or Firm* — LaBatt, LLC

(57) ABSTRACT

A diffusive ultraviolet illuminator is provided. The illuminator can include a reflective mirror and a set of ultraviolet radiation sources located within a proximity of the focus point of the reflective mirror. The ultraviolet radiation from the set of ultraviolet radiation sources is directed towards a reflective surface located adjacent to the illuminator. The reflective surface can diffusively reflect at least 30% the ultraviolet radiation and the diffusive ultraviolet radiation can be within at least 40% of Lambertian distribution. A set of optical elements can be located between the illuminator and the reflective surface in order to direct the ultraviolet radiation towards at least 50% of the reflective surface.

20 Claims, 18 Drawing Sheets

Related U.S. Application Data filed on May 2, 2016, provisional application No. 62/319,752, filed on Apr. 7, 2016.

(51) Int. Cl.

| | | |
|---|---|---|
| *G02B 5/02* | (2006.01) | |
| *G02B 5/08* | (2006.01) | |
| *G02B 5/10* | (2006.01) | |
| *G02B 6/02* | (2006.01) | |
| *G02B 19/00* | (2006.01) | |
| *F21V 8/00* | (2006.01) | |

(52) U.S. Cl.
CPC .............. *G02B 5/0891* (2013.01); *G02B 5/10* (2013.01); *G02B 6/02295* (2013.01); *G02B 19/0023* (2013.01); *G02B 19/0095* (2013.01); *G02B 6/001* (2013.01); *G02B 6/0096* (2013.01)

(56) References Cited

U.S. PATENT DOCUMENTS

| | | |
|---|---|---|
| 8,277,734 B2 | 10/2012 | Koudymov et al. |
| 8,690,409 B2 | 4/2014 | Shin et al. |
| 8,980,178 B2 | 3/2015 | Gaska et al. |
| 9,006,680 B2 | 4/2015 | Bettles et al. |
| 9,034,271 B2 | 5/2015 | Shur et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,550,004 B2 | 1/2017 | Smetona et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,718,706 B2 | 8/2017 | Smetona et al. |
| 9,724,441 B2 | 8/2017 | Shur et al. |
| 9,750,830 B2 | 9/2017 | Shur et al. |
| 9,757,486 B2 | 9/2017 | Dobrinsky et al. |
| 9,795,699 B2 | 10/2017 | Shur et al. |
| 9,801,965 B2 | 10/2017 | Bettles et al. |
| 9,802,840 B2 | 10/2017 | Shturm et al. |
| 9,878,061 B2 | 1/2018 | Shur et al. |
| 9,919,068 B2 | 3/2018 | Shur et al. |
| 9,974,877 B2 | 5/2018 | Bettles et al. |
| 9,981,051 B2 | 5/2018 | Shur et al. |
| 9,987,383 B2 | 6/2018 | Bilenko et al. |
| 9,999,782 B2 | 6/2018 | Shur et al. |
| 10,004,821 B2 | 6/2018 | Dobrinsky et al. |
| 10,040,699 B2 | 8/2018 | Smetona et al. |
| 10,099,944 B2 | 10/2018 | Smetona et al. |
| 2008/0158882 A1* | 7/2008 | Wang ................. G02B 6/003 362/247 |
| 2012/0168641 A1* | 7/2012 | Lizotte ................ A23L 3/28 250/435 |
| 2013/0039050 A1* | 2/2013 | Dau ................. G02B 6/0045 362/218 |
| 2013/0048545 A1 | 2/2013 | Shatalov et al. |
| 2013/0286678 A1 | 10/2013 | Sugiyama et al. |
| 2014/0146521 A1 | 5/2014 | Kim et al. |
| 2014/0183377 A1* | 7/2014 | Bettles ................. A61L 2/10 250/455.11 |
| 2014/0192558 A1* | 7/2014 | Dau ................. G02B 6/0073 362/612 |
| 2014/0202962 A1 | 7/2014 | Bilenko et al. |
| 2015/0060692 A1* | 3/2015 | Chen ................. C02F 1/325 250/435 |
| 2015/0069265 A1* | 3/2015 | Smetona .............. A61L 2/10 250/455.11 |
| 2015/0219833 A1* | 8/2015 | Dau ................. G02B 6/0073 362/606 |
| 2016/0074548 A1 | 3/2016 | Dobrinsky et al. |
| 2016/0114186 A1 | 4/2016 | Dobrinsky et al. |
| 2016/0200594 A1* | 7/2016 | Chen ................. C02F 1/325 250/435 |
| 2017/0057842 A1 | 3/2017 | Dobrinsky et al. |
| 2017/0095585 A1 | 4/2017 | Smetona et al. |
| 2017/0100495 A1 | 4/2017 | Shur et al. |
| 2017/0189711 A1 | 7/2017 | Shur et al. |
| 2017/0212295 A1* | 7/2017 | Vasylyev .............. G02B 6/001 |
| 2017/0245527 A1 | 8/2017 | Dobrinsky et al. |
| 2017/0245616 A1 | 8/2017 | Lakios et al. |
| 2017/0248744 A1 | 8/2017 | Dobrinsky et al. |
| 2017/0281812 A1 | 10/2017 | Dobrinsky et al. |
| 2017/0284933 A1 | 10/2017 | Simin et al. |
| 2017/0320755 A1* | 11/2017 | Chen ................. C02F 1/325 |
| 2018/0364413 A1* | 12/2018 | Dau ................. G02B 6/0073 |

\* cited by examiner

FIG. 1A
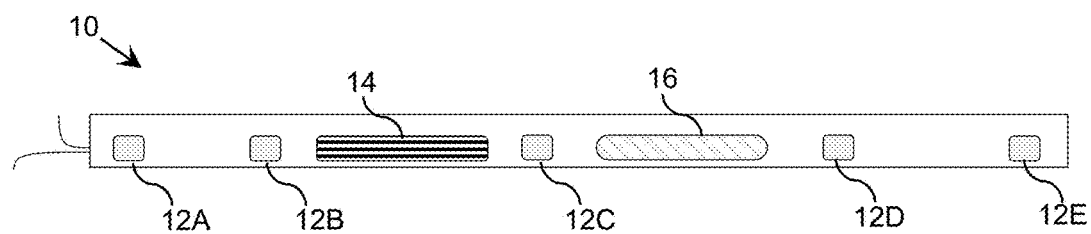
FIG. 1B
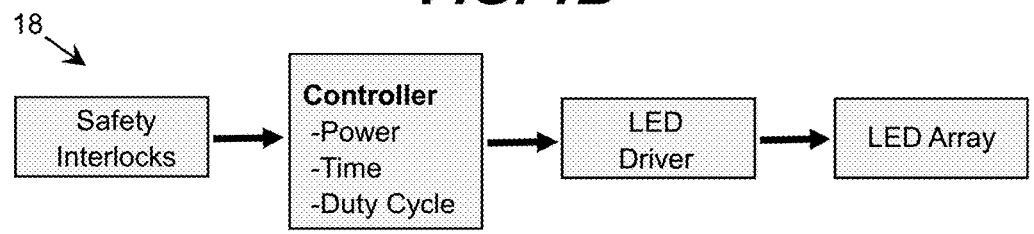
FIG. 1C
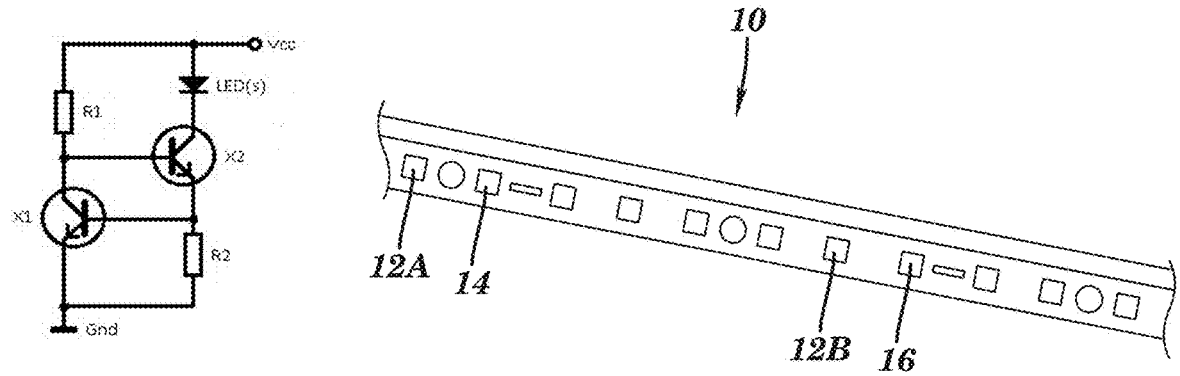
FIG. 1D

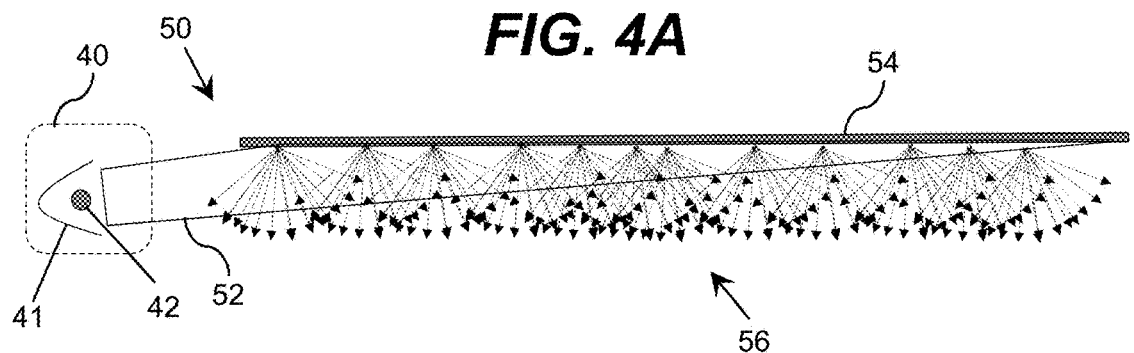
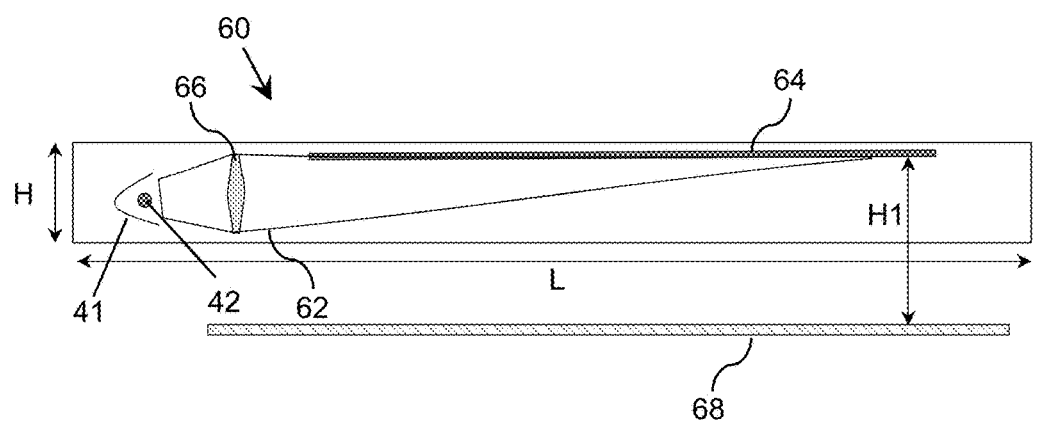
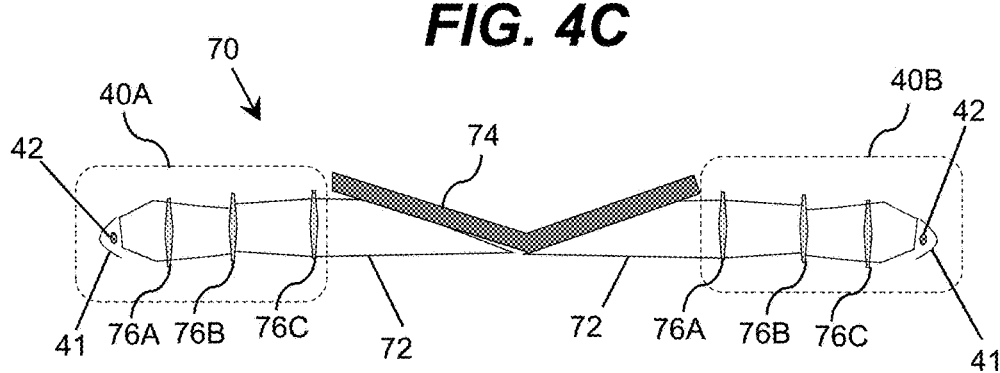

ULTRAVIOLET SURFACE ILLUMINATION SYSTEM

REFERENCE TO RELATED APPLICATIONS

The current application claims the benefit of U.S. Provisional Application No. 62/319,752, filed on 7 Apr. 2016, U.S. Provisional Application No. 62/330,368, filed on 2 May 2016, and U.S. Provisional Application No. 62/356,696, filed on 30 Jun. 2016, all of which are hereby incorporated by reference. Aspects of the current application are related to U.S. application Ser. No. 14/853,075, filed on 14 Sep. 2015, U.S. application Ser. No. 15/472,198, filed on 28 Mar. 2017, U.S. Pat. No. 9,034,271, filed on 28 Aug. 2013, and U.S. Pat. No. 9,550,004, filed on 5 Sep. 2014, all of which are hereby incorporated by reference.

TECHNICAL FIELD

The disclosure relates generally to ultraviolet radiation, and more particularly, to disinfecting a surface using ultraviolet radiation.

BACKGROUND ART

The use of light diffusers is common in backlight illumination, which is frequently used in liquid crystal displays (LCDs). For visible light, the criterion of diffuser design is significantly different than that for ultraviolet (UV) radiation. This is largely related to the fact that UV transparent materials are harder to manufacture than corresponding materials for visible light. Further, the transparency of UV materials is typically inferior to the transparency of materials to visible light. In addition, UV transparent materials are more expensive than the materials transparent to visible light.

Recently, various improvements to backlight visible light illumination design have been proposed. For example, collimating multi-layer optical film (CMOF) provides a cost efficient light management for LCD backlights with integrated optical films. These films provide diffusive capability to LCD backlight illuminators. CMOF is based on multi-layer optical film technology that is used to make current display films, such as dual brightness enhancement film (DBEF), reflective polarizers, and enhanced specular reflector (ESR) films. The CMOFs are used in a new backlight architecture developed by 3M™ and branded as Air Guide. CMOF technology combines two types of nanotechnologies: nanolayer optics and ultra-low refractive index nanofoam. The CMOF film is attached directly to the LCD panel, replacing several separate films used in current light emitting diode (LED) backlight designs. The new design uses a hollow cavity with no free-floating films and no solid light guide. In the Air Guide design, light is spread through the air of the cavity between the LCD panel and the highly reflective film.

In another traditional design for diffusive wave guiding, the LED lights are positioned at a side of the diffuser. The diffuser is composed of several layers: a sheet with microfeatures, reflecting and light guiding sheets, and a diffusive sheet followed by optional prismatic and other diffusive sheets. For success of such a design, good light reflective and light transparent materials have to be employed, which is difficult to achieve for ultraviolet illumination.

SUMMARY OF THE INVENTION

The present invention considers another design utilizing scattering surfaces for uniform UV illumination.

Aspects of the invention provide an ultraviolet diffusive illuminator. The illuminator includes a reflective mirror and a set of ultraviolet radiation sources located within a proximity of the focus point of the reflective mirror. The ultraviolet radiation from the set of ultraviolet radiation sources is directed towards a reflective surface located adjacent to the illuminator. The reflective surface diffusively reflects at least 30% the ultraviolet radiation and the diffusive ultraviolet radiation is within at least 40% of Lambertian distribution. A set of optical elements can be located between the illuminator and the reflective surface in order to direct the ultraviolet radiation towards at least 50% of the reflective surface.

A first aspect of the invention provides a system comprising: an illuminator including: a reflective mirror; and a set of ultraviolet radiation sources located within a proximity of a focus point of the reflective mirror, the set of ultraviolet radiation sources configured to generate ultraviolet radiation directed at the reflective mirror; a reflective surface located adjacent to the illuminator; and a set of optical elements located between the illuminator and the reflective surface, the set of optical elements configured to direct an ultraviolet radiation beam towards at least 50% of the reflective surface, wherein the reflective surface diffusively reflects at least 30% of the ultraviolet radiation.

A second aspect of the invention provides a system comprising: an illuminator including: a reflective mirror; and a set of ultraviolet radiation sources located within a proximity of a focus point of the reflective mirror, the set of ultraviolet radiation sources configured to generate ultraviolet radiation directed at the reflective mirror; a reflective surface located adjacent to the illuminator; and a set of optical elements located between the illuminator and the reflective surface, the set of optical elements configured to direct an ultraviolet radiation beam towards at least 50% of the reflective surface, wherein the reflective surface diffusively reflects the ultraviolet radiation to within 40% of Lambertian distribution.

A third aspect of the invention provides a system comprising: a set of illuminators, each illuminator including: a reflective mirror; and a set of ultraviolet radiation sources located within a proximity of a focus point of the reflective mirror, the set of ultraviolet radiation sources configured to generate ultraviolet radiation directed towards the reflective mirror; a reflective surface located between the set of illuminators; and a set of optical elements located between each illuminator and the reflective surface, the set of optical elements configured to direct an ultraviolet radiation beam towards at least 50% of the reflective surface, wherein the reflective surface diffusively reflects the ultraviolet radiation to within 40% of Lambertian distribution.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 1A shows an illustrative illuminator according to an embodiment, FIG. 1B shows an illustrative electrical system, FIG. 1C shows an illustrative electrical diagram, and FIG. 1D shows a prototype of an illuminator according to an embodiment.

FIGS. 3A and 3B show an illustrative illuminator according to an embodiment, while

FIGS. 4A-4C show illustrative systems according to embodiments.

FIG. 20A shows an illustrative illuminator according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 2A:
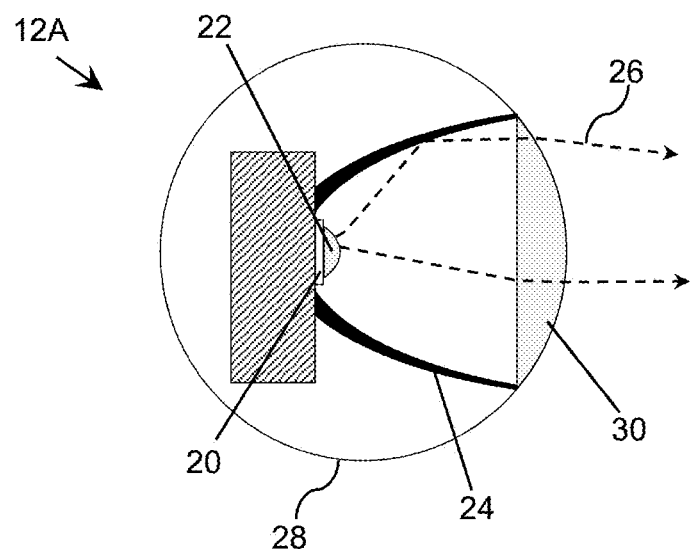
FIGS. 2A and 2B show illustrative ultraviolet radiation sources according to embodiments.

As indicated above, aspects of the invention provide an ultraviolet diffusive illuminator. The illuminator includes a reflective mirror and a set of ultraviolet radiation sources located within a proximity of the focus point of the reflective mirror. The ultraviolet radiation from the set of ultraviolet radiation sources is directed towards a reflective surface located adjacent to the illuminator. The reflective surface diffusively reflects at least 30% the ultraviolet radiation and the diffusive ultraviolet radiation is within at least 40% of Lambertian distribution. A set of optical elements can be located between the illuminator and the reflective surface in order to direct the ultraviolet radiation towards at least 50% of the reflective surface.

As used herein, unless otherwise noted, the term "set" means one or more (i.e., at least one) and the phrase "any solution" means any now known or later developed solution. It is understood that, unless otherwise specified, each value is approximate and each range of values included herein is inclusive of the end values defining the range. As used herein, unless otherwise noted, the term "approximately" is inclusive of values within +/-ten percent of the stated value, while the term "substantially" is inclusive of values within +/-five percent of the stated value. Unless otherwise stated, two values are "similar" when the smaller value is within +/-twenty-five percent of the larger value.

Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength and is highly reflective when the material/structure has an ultraviolet reflection coefficient of at least seventy percent. Furthermore, a material/structure is considered to be "transparent" to ultraviolet light of a particular wavelength when the material/structure allows at least ten percent of the ultraviolet light, which is radiated at a normal incidence to an interface of the layer, to pass there through; highly transparent when at least thirty percent of the radiation passes there through; and substantially transparent when at least eighty percent of the radiation passes there through. In an embodiment, the target wavelength of the radiation corresponds to a wavelength of radiation emitted or sensed (e.g., peak wavelength +/-five nanometers) by an active region of an optoelectronic device during operation of the device.

Turning to the drawings, FIG. 1A shows an illustrative illuminator 10 according to an embodiment. Although the illuminator 10 is shown as an elongated lamp, it is understood that this is for exemplary purposes only and that the illuminator 10 can be any shape. The illuminator 10 includes a set ultraviolet radiation sources 12A-12E, each of which can be positioned at any location on the illuminator 10. The illuminator 10 can also include a set of sensors 14, 16. The set of ultraviolet radiation sources 12A-12E can comprise any combination of one or more ultraviolet radiation emitters. Examples of ultraviolet radiation emitters can include, but are not limited to, high intensity ultraviolet lamps (e.g., high intensity mercury lamps), discharge lamps, ultraviolet LEDs, super luminescent LEDs, laser diodes, and/or the like. In one embodiment, the set of ultraviolet radiation sources 12A-12E can include a set of LEDs manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the set of ultraviolet radiation sources 12A-12E can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a waveguide, a plurality of ultraviolet fibers, each of which terminates at an opening, a diffuser, a light guiding layer, a light diffusing layer, and/or the like.

It is understood that the number of ultraviolet radiation sources 12A-12E illustrated in FIG. 1A and the other embodiments depicted in the remaining figures is only illustrative. Those skilled in the art will appreciate that any number of one or more ultraviolet radiation sources may be located within the illuminator 10.

Each of the ultraviolet radiation sources 12A-12E can operate at the same or different wavelengths. For example, one or more of the ultraviolet radiation sources 12A-12E can have a peak emission of approximately 280 nanometers (nm), while the remaining ultraviolet radiation sources 12A-12E have a peak emission of approximately 295 nm.

FIG. 1B shows an illustrative electrical system 18 for an illuminator, such as the illuminator 10 shown in FIG. 1A, according to an embodiment. The electrical system 18 is configured to deliver a controlled power supply to the set of ultraviolet radiation sources 12A-12E in order to adjust a plurality of attributes of the ultraviolet radiation. For example, the wavelength, intensity, duty cycle, duration, and/or the like, of each of the set of ultraviolet radiation sources 12A-12E can be independently adjusted. Although it is not shown, it is understood that the illuminator 10 can include a set of sensors (e.g., fluorescent, temperature, humidity, and/or the like) and visible cameras 14, 16 in order to monitor a surface and/or an object located on the surface. The electrical system 18 can include an electrical transforming device that can transform a regular alternating current power source to a direct current power source. As shown in FIG. 1B, the electrical system 18 can also include safety interlocks in order to manually shut down power and protect a user from electrical shock, a controller to adjust the power, time, duty cycle, and/or the like, for each of the set of ultraviolet radiation sources 12A-12E (FIG. 1A), and an LED driver controlled by the controller in order to deliver power to the set of ultraviolet radiation sources 12A-12E according to the target requirements for each ultraviolet radiation source 12A-12E. FIG. 1C shows an illustrative electrical diagram of the system 18 shown in FIG. 1B. FIG. 1D shows an illustrative prototype of the illuminator 10 shown in FIG. 1A. In an embodiment, the sensor 14 can be a fluorescent sensor, infrared sensor, and/or can comprise a visible camera. In an embodiment, the sensor 16 can comprise a source of UV-A, deep blue or visible light. It is understood that the illuminator 10 can comprise a data processing unit capable of analyzing the sensed radiation and adjusting power of the ultraviolet radiation sources to achieve the objective of the illumination, wherein the objective can be a required intensity of radiation, a set radiation dose at a target wavelength, and/or control of biological dynamics, such as elimination of bacteria, viruses, and/or mildew.

Figure 2B:
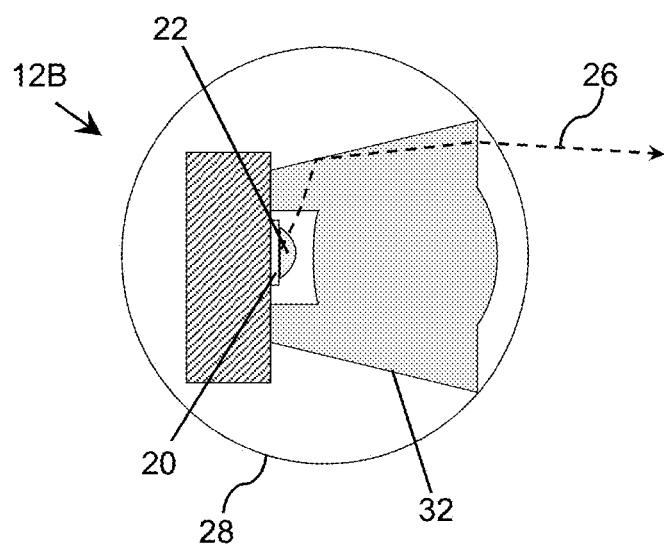

FIGS. 2A and 2B show illustrative ultraviolet radiation sources 12A, 12B according to embodiments. In FIG. 2A, the ultraviolet radiation source 12A includes an ultraviolet LED emitter 20 and an optical element 22 directly bonded to a light emitting surface of the ultraviolet LED emitter 20. The ultraviolet radiation source 12A can also include a reflective mirror 24 that is shaped to deliver a target distribution of intensity for the ultraviolet radiation 26. In an embodiment, the reflective mirror 24 can be a parabolic reflector. In another embodiment, the reflective mirror 24 can be a conical reflector. The reflective mirror 24 can be formed of any reflective material, such as highly polished aluminum, fluoropolymer, such as polytetrafluoroethylene (PTFE, such as Teflon®), and/or the like, in order to direct the ultraviolet radiation 26 out of the cylindrical enclosure 28 that encompasses the components of the ultraviolet radiation source 12A. The cylindrical enclosure 28 is transparent to ultraviolet radiation and is formed of an ultraviolet transparent material, such as a fluoropolymer, silicon dioxide ($SiO_2$), and/or the like. In an embodiment, only a part of the cylindrical enclosure 28 is transparent to ultraviolet radiation. For example, the cylindrical enclosure 28 can comprise an ultraviolet reflective enclosure 28 having an ultraviolet transparent window. The enclosure 28 can comprise a reflective material such as aluminum, fluoropolymer, and/or the like, while the ultraviolet transparent window can comprise an ultraviolet transparent material, such as fluoropolymer, silicon dioxide ($SiO_2$), sapphire, calcium fluoride ($CaF_2$), magnesium fluoride ($MgF_2$), and/or the like. A lens element 30 can be located at a light emitting end of the reflective mirror 24 and can be used to further direct the ultraviolet radiation 26 emitted from the ultraviolet radiation source 12A.

In an embodiment, as shown in the ultraviolet radiation source 12B in FIG. 2B, a total internal reflection (TIR) lens 32 can be used to direct the ultraviolet radiation 26. A TIR lens 32 can be beneficial to the overall design of the ultraviolet radiation source 12B due to the low losses as compared to a reflective mirror. Regardless, in any embodiment, the lenses 30, 32 can be formed of an ultraviolet transparent material, such as silicon dioxide ($SiO_2$), sapphire, calcium fluoride ($CaF_2$), magnesium fluoride ($MgF_2$), anodized aluminum oxide (AAO), and/or the like. In an embodiment, the TIR lens 32 can comprise a fluoropolymer that is transparent to ultraviolet radiation. For example, the TIR lens 32 can comprise a fluoropolymer that is at least 50% transparent to ultraviolet radiation. In an embodiment, some portion of the lens 30 in the ultraviolet radiation source 12A and/or the lens 32 in the ultraviolet radiation source 12B can include Fresnel lenses. For example, the concave portions of the lens 30, 32 can be replaces by Fresnel lens. The table (Table 1) below shows exemplary power intensities for an ultraviolet radiation source at specific distances from the surface of an LED die. For example, the ultraviolet radiation source can operate at about 6-10 microwatts/$cm^2$ at a distance of approximately 10 cm.

TABLE 1

| Distance (cm) | Average Power Intensity (uW/$cm^2$) | Standard Deviation |
|---|---|---|
| 10 | 6-10 | 0.2-1 |
| 20 | 2-5 | 0.1-0.2 |
| 30 | 0.5-3 | 0.05-0.15 |

Figure 3A:
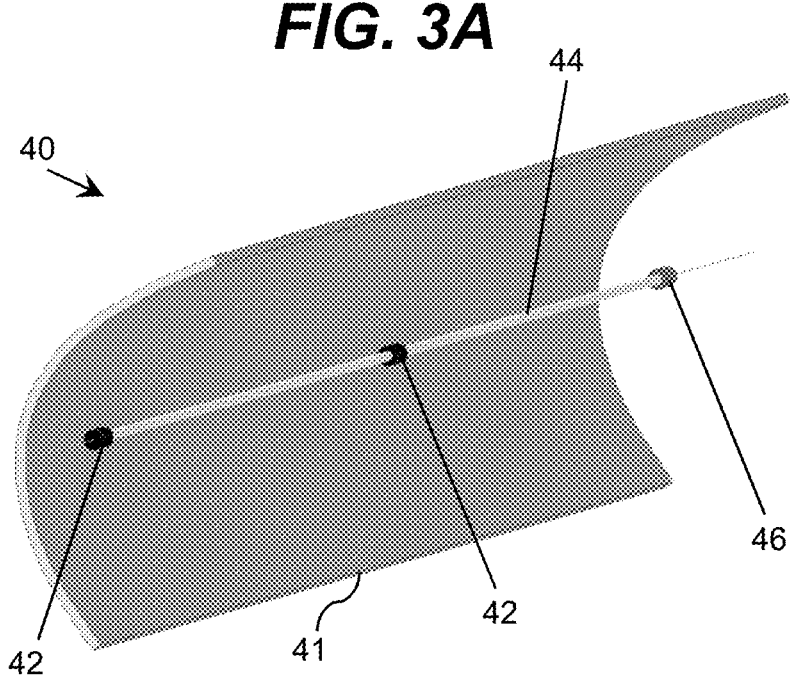
Figure 3B:
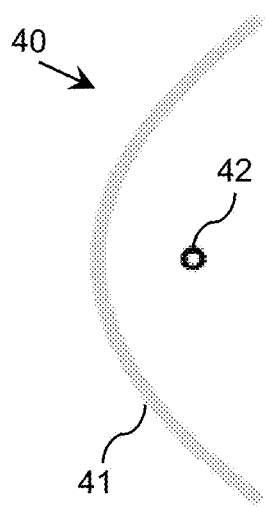
Figure 3C:
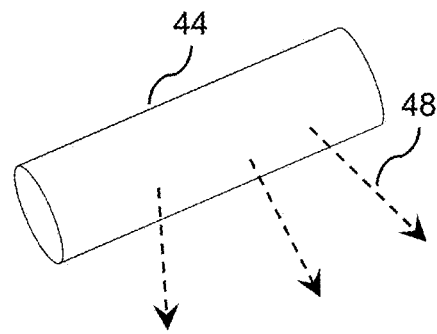
FIG. 3C shows an illustrative waveguide according to an embodiment.

Turning now to FIG. 3A, an illustrative illuminator 40 according to an embodiment is shown. The illuminator 40 can comprise a parabolic body 41 and a set of ultraviolet radiation sources 42 located in the proximity of a focus point of the parabolic body 41. The precision of positioning the set of ultraviolet radiation sources 42 within a focal point can affect the direction of the radiated light. The precise positioning of the set of ultraviolet radiation sources 42 can be adjusted depending on the distribution of the intensity at the target surface away from the illuminator 40. The parabolic body 41 can include a cylinder with a two dimensional parabolic cross section. FIG. 3B shows a side view of the illuminator 40 including the parabolic body 41 and a set of ultraviolet radiation sources 42 located at the focus point. In an embodiment, the set of ultraviolet radiation sources 42 can be coupled to a diffusive waveguide 44. As shown in FIG. 3C, the diffusive waveguide 44 can be configured to radiate ultraviolet radiation 48 from the set of ultraviolet radiation sources 42 by leaking it out of the diffusive surface.

The diffusive waveguide 44 can be formed of an ultraviolet transparent material, such as $SiO_2$, fluoropolymer, $CaF_2$, $MgF_2$, and/or the like. In an embodiment, the diffusive waveguide 44 includes a plurality of roughness elements on a surface that are configured to emit uniform ultraviolet radiation through the waveguide 44. The plurality of roughness elements 44 can be micro-crystals or micro-domains of ultraviolet transparent material, such as $SiO_2$, sapphire, $CaF_2$, $MgF_2$, AAO, and/or the like. In an embodiment, the diffusive waveguide 44 can contain vacancies that are filled with a liquid, such as water. The water can include diffusive domains that are configured to scatter radiation. In an embodiment, at least one sensor 46 (e.g., an ultraviolet LED sensor) can be coupled to the diffusive waveguide 44. The parabolic body 41 is formed of a highly reflective material, such as polished aluminum, and/or the like. In an embodiment, the parabolic body 41 has a high specular reflectivity to ultraviolet radiation, wherein high means at least 70% specularly reflective.

Turning now to FIG. 4A, an illustrative system 50 including an illuminator, such as the illuminator 40 shown in FIG. 3A, according to an embodiment is shown. However, it is understood that the system 50 can include any of the embodiments of the illuminator described herein. Regardless, as discussed in conjunction with FIG. 3A, the illuminator 40 includes a parabolic body 41 and a set of ultraviolet radiation sources 42 located at or in the proximity of the focus point of the parabolic body 41 in order to form a collimated beam of ultraviolet radiation 52. It is understood that the collimated beam of ultraviolet radiation 52 is not perfectly collimated and the degree of collimation depends on the target application of the illuminator 40. In an embodiment, the illuminator 40 is configured to direct the collimated beam of ultraviolet radiation 52 to impinge on a reflective surface 54 and cover at least 50% of the reflective surface 54. It is understood that this can be accomplished by adjusting the attributes of the illuminator 40 (e.g., how the ultraviolet radiation 52 is reflected from the parabolic body 41) and/or by changing the direction/angle of the illuminator 40. In an embodiment, the direction of the collimated beam of ultraviolet radiation 52 is substantially tangential with the reflective surface 54. The reflective surface 54 can be formed of a highly diffusively reflective material, such as a fluoropolymer, such as polytetrafluoroethylene (PTFE, such as Teflon®), rough aluminum, rough sapphire, rough $SiO_2$/aluminum mirror, fluorinated ethylene propylene co-polymer (EFEP), ethylene tetrafluoroethylene (ETFE), expanding polytetrafluoroethylene (ePTFE) membrane (e.g., GORE® DRP® Diffuse Reflector Material), and/or the like. In an embodiment, the reflective surface 54 reflects at least 30% of the ultraviolet radiation 52. In a more specific embodiment, the reflective surface 54 reflects at least 50% of the ultraviolet radiation 52. The reflective surface 54 is configured to provide a uniform diffusive reflection 56. The uniform diffusive reflection 56 is within at least 40% of a Lambertian distribution.

It is understood that the position and direction of the collimated beam of ultraviolet radiation 52 can be varied to provide a uniform diffusive reflection 56 off of the reflective surface 54. However, a system can also include additional optical elements to control and direct the ultraviolet radiation. For example, FIG. 4B shows an illustrative system 60 according to an embodiment. In the system 60, a set of lenses 66 can be used to direct the collimated beam of ultraviolet radiation 62 at the reflective surface 64. Although only one lens 66 is shown, it is understood that the system 60 can include any number of lenses. In an embodiment, it is understood that any and all of the lenses can be removed and the system 60 can remain operational. Each lens in the set of lenses 66 has a focal length that is comparable to the diameter of the collimated beam of ultraviolet radiation 62. In an embodiment, the diffusive reflection 56 (FIG. 4A) off of the reflective surface 64 is uniform over at least 20% of a target surface 68, which is located a distance H1 away from the reflective surface 64. In an embodiment, the illuminator can comprise height H and width L and can be designed such that overall illuminator volume is small. In an embodiment, H is smaller than L and can be at most 10% of L for an illuminator that designed to irradiate a large area without taking significant amount of physical space. In an embodiment, with the distance H1 between the reflective surface 64 and the target surface 68 as a known parameter, the diffusive and/or reflective properties of the reflective surface 64 can vary laterally in order to provide a more uniform diffusive reflection 56 (FIG. 4A). Other aspects of the system 60 can be changed to improve the uniformity of the diffusive reflection 56, including, but not limited to, the direction of the collimated beam of ultraviolet radiation 62 (e.g., by changing the direction of the illuminator 40), the position and/or orientation of optical elements within the system 60, such as the lens 66, and/or the like. In an embodiment, the diffusive reflection 56 can be variable by changing the orientation of the illuminator 40 so that the collimated beam of ultraviolet radiation 62 is only directed at a portion of the reflective surface 64.

FIG. 4C shows an illustrative system 70 including a first illuminator 40A and a second illuminator 40B according to an embodiment. Similar to the illuminator 40 shown in FIG. 3A, each of the illuminators 40A, 40B includes a parabolic body 41 and a set of ultraviolet radiation sources 42 located in or in the proximity of the focus point of the parabolic body 41 in order to form a collimated beam of ultraviolet radiation 46. Each illuminator 40A, 40B also includes a set of lenses 76A-C that are configured to further collimate the ultraviolet radiation 72 and direct it towards a reflective surface 74. The reflective surface 74 can be similar to the reflective surfaces 54, 64 shown in FIGS. 4A and 4B and can be formed of a highly diffusively reflective material, such as a fluoropolymer, such as polytetrafluoroethylene (PTFE, such as Teflon®), rough aluminum, fluorinated ethylene propylene co-polymer (EFEP), ethylene tetrafluoroethylene (ETFE), expanding polytetrafluoroethylene (ePTFE) membrane (e.g., GORE® DRP® Diffuse Reflector Material), and/or the like. The reflective surface 74 can reflect at least 50% of the ultraviolet radiation 72. In this embodiment, instead of changing an angle of the illuminators 40A, 40B, the reflective surface 74 is substantially a V-shape, so that the collimated beam of ultraviolet radiation 72 from each illuminator 40A, 40B can be directed at the reflective surface 74. It is understood a system can include more than two illuminators and the reflective surface can include additional facets/surfaces in order to diffusively reflect the ultraviolet radiation of each illuminator.

Figure 5A:
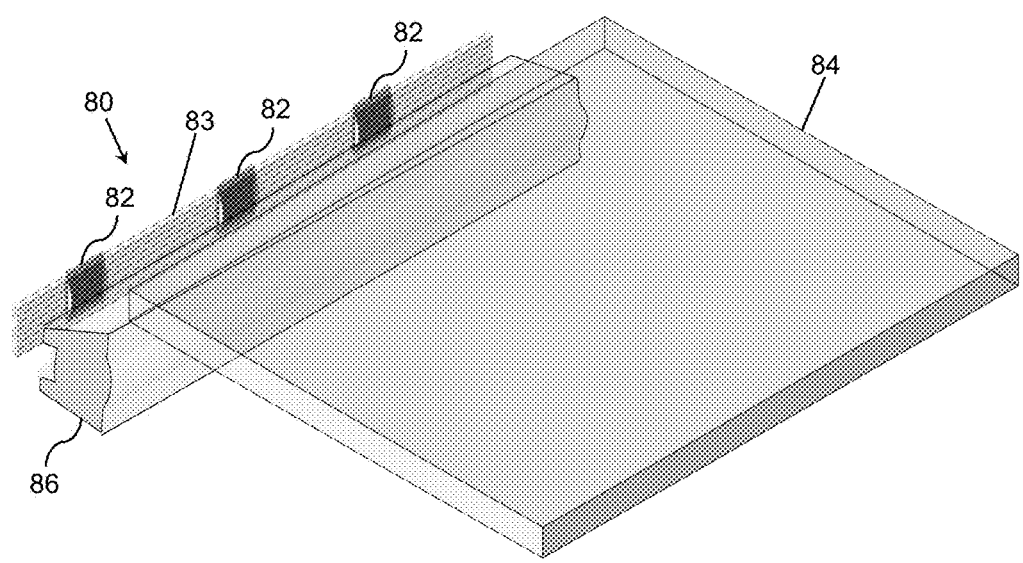
FIGS. 5A and 5B show illustrative illuminators according to embodiments.
Figure 5B:
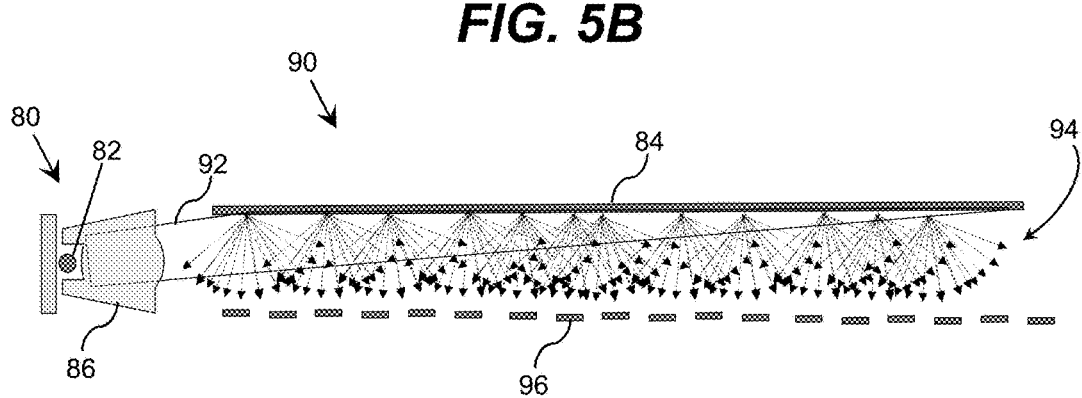

FIG. 5A shows a three-dimensional view of an illustrative illuminator 80 with a reflective surface 84 according to an embodiment, while FIG. 5B shows an illustrative system 90 including the illuminator 80 according to an embodiment. The illuminator 80 includes a set of ultraviolet radiation sources 82 that can be coupled to a diffusive waveguide 83, similar to the diffusive waveguide 44 shown in FIG. 3A. Although only three ultraviolet radiation sources 82 are shown in FIG. 5A, it is understood that the illuminator 80 can include any number of ultraviolet radiation sources. Referring now to FIGS. 5A and 5B, in an embodiment, the set of ultraviolet radiation sources 82 can be located adjacent to an elongated TIR lens 86 that is configured to form a collimated beam of ultraviolet radiation 92 from the set of ultraviolet radiation sources 82 onto a reflective surface 84 to provide a diffusive reflection 94. In an embodiment, the system 90 can also include a mesh 96 that is configured to promote diffusive scattering and recycling of the ultraviolet radiation. The mesh 96 is formed of an ultraviolet reflective material and can include aluminum, PFTE (e.g., Teflon®) and/or the like. The spacing of the portions of the mesh 96, and the structure of the mesh 96 is selected to form a uniform radiation over the target surface within at least 50% of the area covered by the illuminator 80, wherein the uniformity means that the difference in intensity of radiation of maximum and minimum intensity values does not exceed 50%. In an embodiment, the mesh 96 can include a photo-catalyst film, such as titanium dioxide ($TiO_2$) that can improve disinfection of the ambient when exposed to ultraviolet radiation, aid in the elimination of unwanted odors present in the ambient, and/or the like. The photo-catalyst film can be selected and radiated by UVA radiation, as UVA radiation (e.g., wavelengths less than approximately 390 nm) is efficiently absorbed by typical photo-catalysts ($TiO_2$). UVA ultraviolet radiation sources can be generated using methods in the visible LED technology, and, as known in the art, UVA devices have significant advantages in reliability power and efficiency.

Figure 6A:
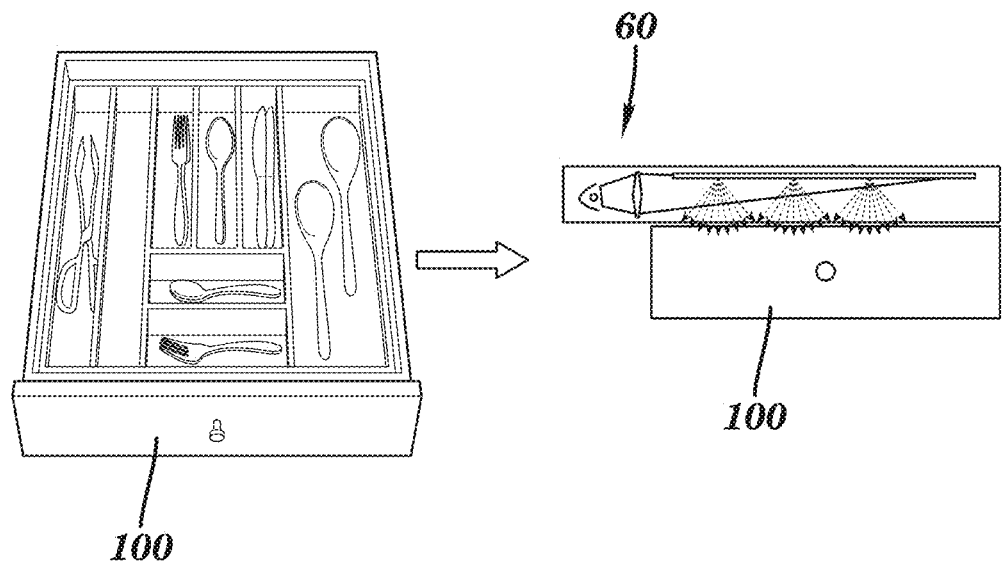
FIGS. 6A and 6B show illustrative devices including an illuminator according to embodiments.
Figure 6B:
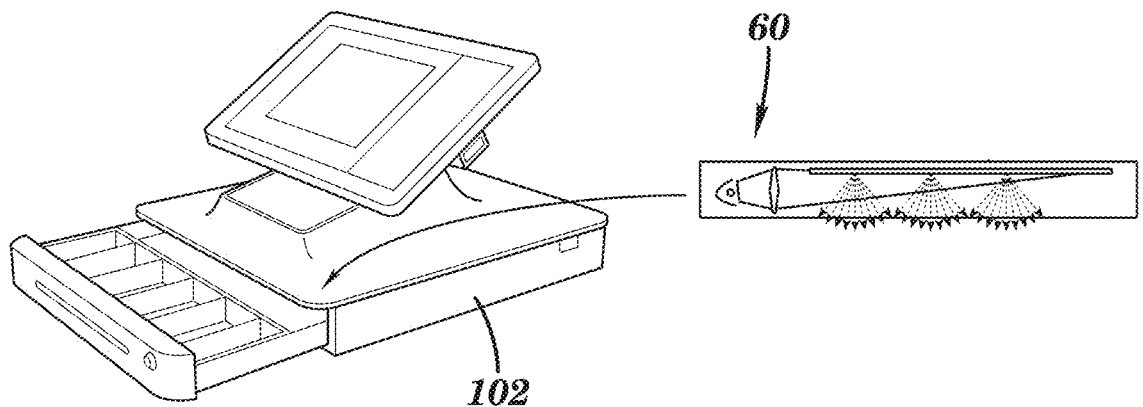

FIGS. 6A and 6B show illustrative devices including an illuminator according to embodiments. FIG. 6A shows a drawer 100 including a system 60 (as shown in FIG. 4B) configured to disinfect the interior of the drawer 100. FIG. 6B shows a cash register 102 including a system 60 configured to disinfect the interior of the cash register 102. In both embodiments, the illuminator in the system 60 is capable of a small height (e.g., H in FIG. 4B) and a large length (e.g., L in FIG. 4B). It is understood that the system 60 illustrated in FIGS. 6A and 6B is only illustrative and the devices 100, 102 can include any embodiment of the systems described herein.

Figure 7:
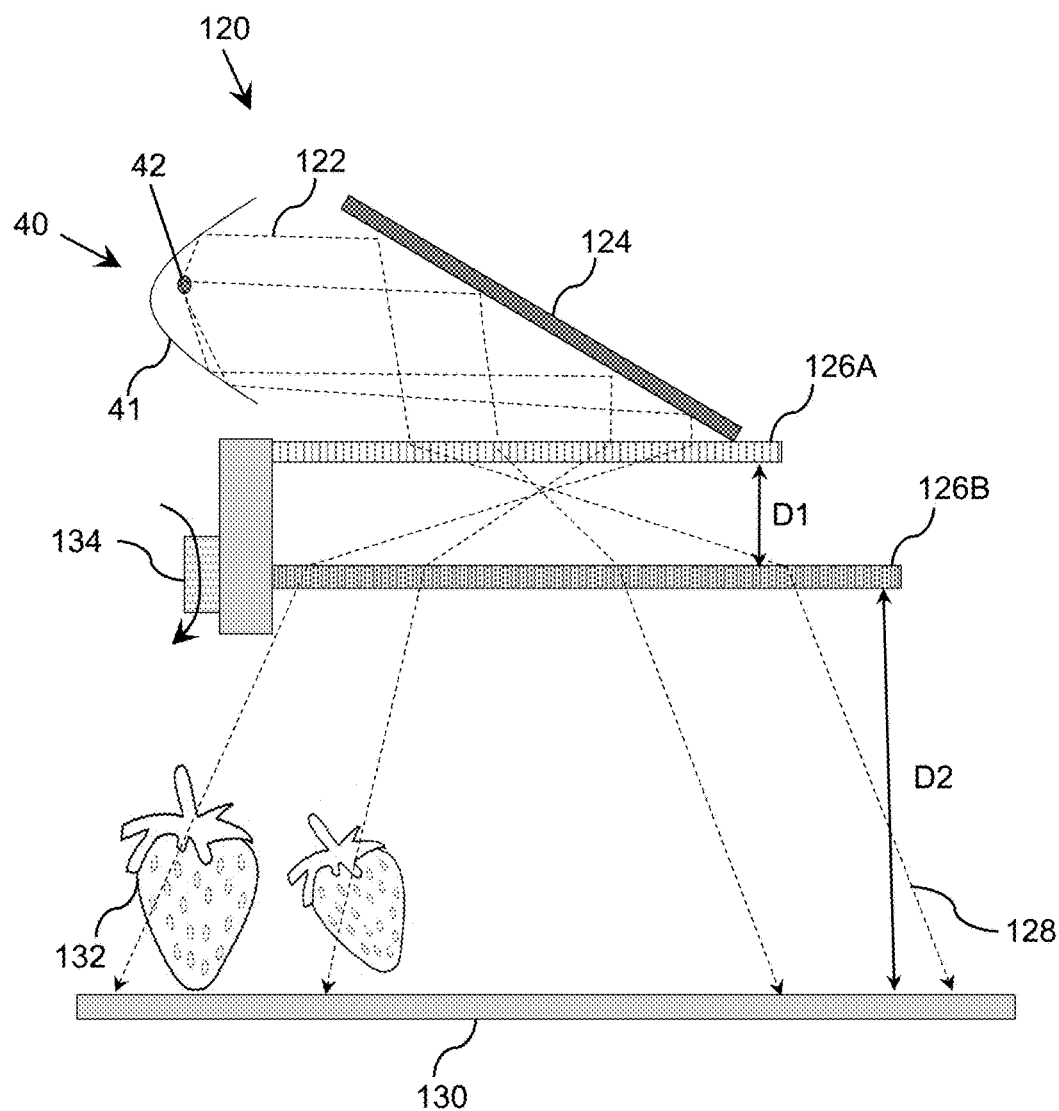
FIG. 7 shows an illustrative system according to an embodiment.

In an embodiment, the orientation of the optical elements with respect to one another in an illuminator can be changed. For example, FIG. 7 shows an illustrative system 120 according to an embodiment. The illuminator 40 is similar to the illuminator shown in FIG. 3A and includes a parabolic body 41 and a set of ultraviolet radiation sources 42 located in a focus point of the parabolic body 41. However, the system 120 includes a reflective surface 124 that is located at an angle in order to reflect the ultraviolet radiation 122 from the illuminator 40 towards a set of lenses 126A, 126B. Although only two lenses 126A, 126B are shown, it is understood that the system 120 can include any number of lenses. The set of lenses 126A, 126B are separated by a distance D1 and the second lens 126B is separated from a target surface 130 by a distance D2. The set of lenses 126A, 126B can be formed of an ultraviolet transparent material such as sapphire, $SiO_2$, a fluoropolymer, calcium fluoride ($CaF_2$), magnesium fluoride ($MgF_2$), anodized aluminum oxide (AAO), and/or the like.

Figure 8:
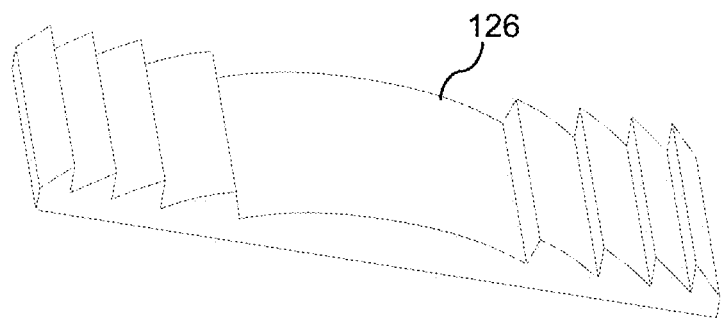
FIG. 8 shows an example of a Fresnel lens.

If the set of lenses 126A, 126B are formed of a fluoropolymer material, the set of lenses 120A, 120B can be Fresnel lenses that are manufacturing through imprinting. An example of a Fresnel lens 126 is shown in FIG. 8. This Fresnel lens 126 is profiled in one direction.

Figure 9A:
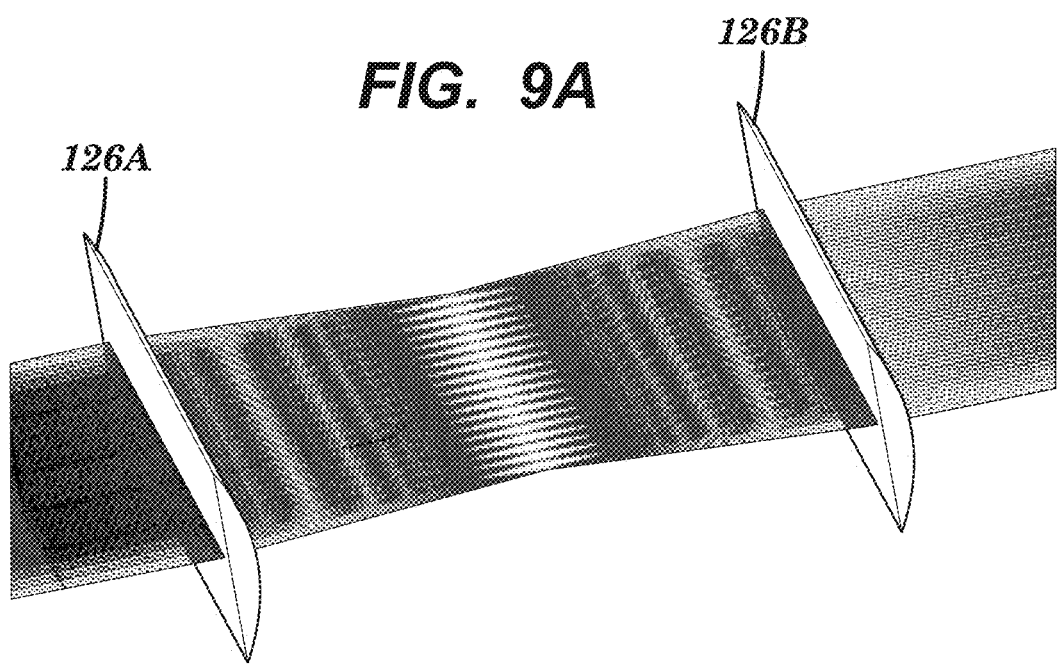
FIGS. 9A and 9B show an illustrative schematic of two lenses within an illuminator according to an embodiment.
Figure 9B:
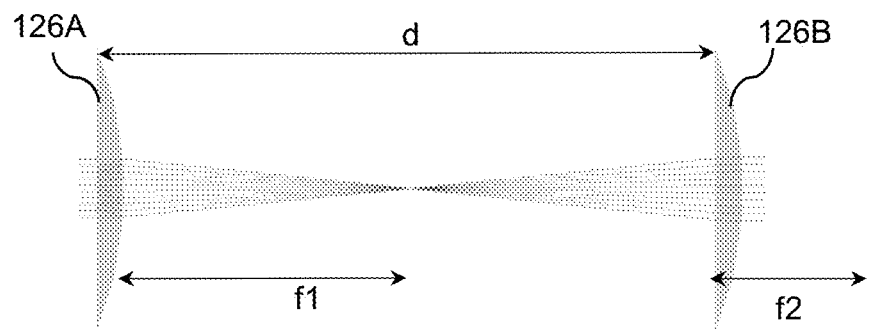
Figure 10:
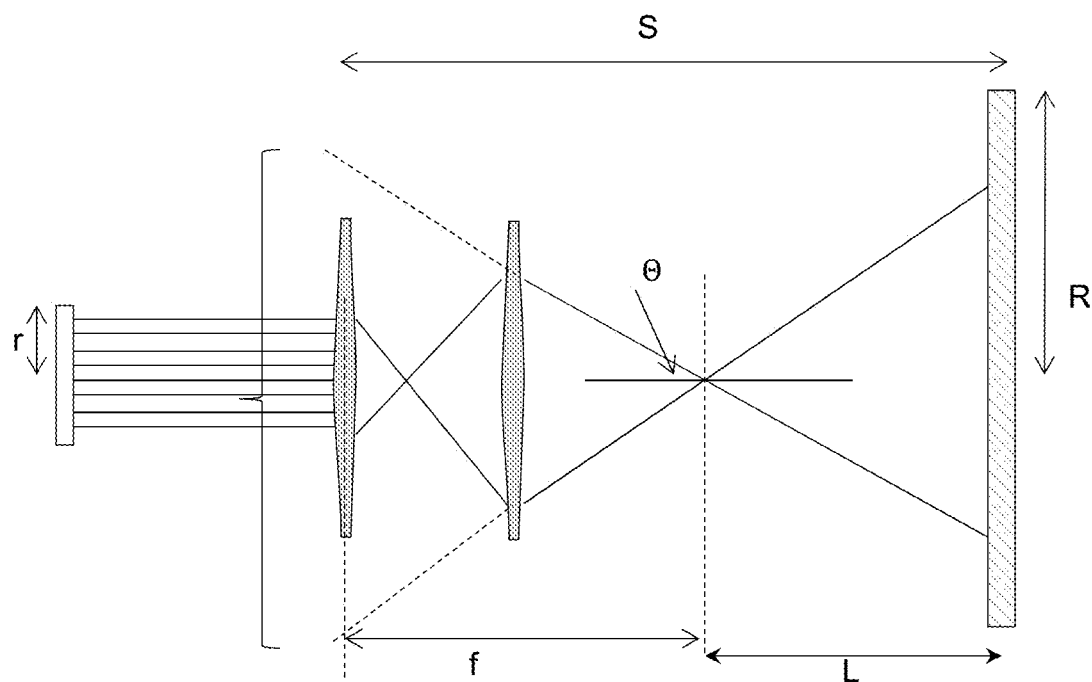
FIG. 10 shows a schematic of two lenses within an illuminator.

Returning to FIG. 7, the distances D1, D2 can vary by moving the position of the second lens 126B with respect the first lens 126A and the target surface 130. In an embodiment, the second lens 126B can be moved using a knob 134. However, it is understood that the knob 134 is for exemplary purposes only and that the second lens 126B can be moved using any method. The system 120 can be designed to be installed along with the target surface 130 (e.g., a shelf) in order to disinfect and/or preserve the target surface 130 and a set of items 132 located on the target surface 130 using the reflected ultraviolet radiation 128 from the set of lenses 126A, 126B. By adjusting the knob 134, the reflected ultraviolet radiation 128 can be uniform across the target surface 130. In an embodiment, adjusting the knob 134 results in a resolution of at least 1 mm. In an embodiment, the target intensity variation does not exceed 50% over the target surface 130. In an embodiment, for the preservation of plants, the system 120 can operate at wavelengths between approximately 280 nm and approximately 310 nm, and for the disinfection purposes, the system 120 can operate at wavelengths between approximately 210 nm and approximately 280 nm. FIGS. 9A and 9B show the two illustrative lenses 126A, 126B from FIG. 7 according to an embodiment. The total focal length of both lenses 126A, 126B is given by the equation: $1/f=1/f_1+1/f_2-d/(f_1 f_2)$, where f is the total focal length of both lenses, $f_1$ is the focal length of the first lens 126A, $f_2$ is the focal length of the second lens 126B, and d is the distance between the two lenses 126A, 126B. It is clear that for $f_1=f_2$, and $d=2f_1$ the resulting light exiting the two lenses is parallel, whereas for $d=f_1$ the two lens structure has the same focal point as a single lens. From this, it follows that the two lens structure can yield high focusing sensitivity for cases when $f_1$ is small, such as $f_1 \sim 1$ cm. Turning to FIG. 10, an illustrative schematic of two lenses according to an embodiment is shown. Consider a distance between an ultraviolet radiation source and a target surface being S (e.g., S can be ½ meter). The radius of the beam r is significantly smaller (on the order of 1 cm). In general, the angle θ can vary between approximately 20 degrees to approximately 60 degrees. In all cases:

$$\frac{R}{L} = \tan\theta,$$

with tan θ~0.2 ... 2 with L~{R/0.2 ... R/2}. Therefore, in general, L~R. Since the focal point distance f is comparable to r (at least for the single lens, and θ=45 degrees), S~L. By placing the second lens (having the same focal distance) in the focal point of the first lens, this produces no effect of the second lens: Consider:

$$\frac{1}{f} = \frac{1}{f_1} + \frac{1}{f_1} - \frac{f_1}{f_1 f_1} = \frac{1}{f_1}.$$

Therefore, the second lens makes no effect and no additional focusing is required. Placing the second lens at a distance $2f_1$ produces a parallel beam:

$$\frac{1}{f} = \frac{1}{f_1} + \frac{1}{f_1} - \frac{2f_1}{f_1 f_1} = 0.$$

Therefore, moving a lens one focal point of the first lens changes the focus from purely defocused to purely focused. Choosing a lens with sufficient small focus length (e.g., f~r~1/cm) allows small changes in the motion of the second lens to lead in large focusing effects of the intensity. Use of a single lens does not allow such sensitivity of focusing, requiring the lens to move on the order L to yield correct focusing. It is important to choose a lens with a sufficiently small focal length (e.g., f~1 cm).

Figure 11:
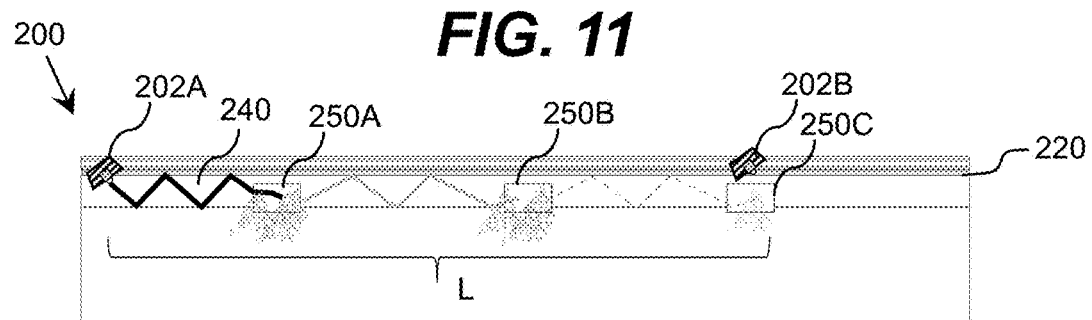
FIG. 11 shows an illustrative waveguide according to an embodiment.

It is understood that other embodiments of a diffusive waveguide can be located in the proximity of the focus point of a parabolic body. FIG. 11 shows an illustrative waveguide 200 according to an embodiment. The waveguide 200 comprises a set of ultraviolet radiation sources 202A, 202B, a reflective layer 220, a propagating region 240, and a plurality of highly diffusive regions 250A-C. The propagation region 240 can comprise an ultraviolet transparent material such as fluoropolymer, $SiO_2$, $Al_2O_3$, $CaF_2$, $MgF_2$, and/or the like. It is understood that the waveguide 200 can be non-uniform in propagating and diffusive characteristics. In an embodiment, the waveguide 200 can include a set of mirror elements. For example, the waveguide 200 can include a parabolic body in one of the layers. The distance L between two sources 202A, 202B is selected to be smaller than the attenuation distance within the propagating region 240, wherein attenuation distance is a distance from the source 202A, 202B where the intensity of light is decreased by 60%.

Figure 12:
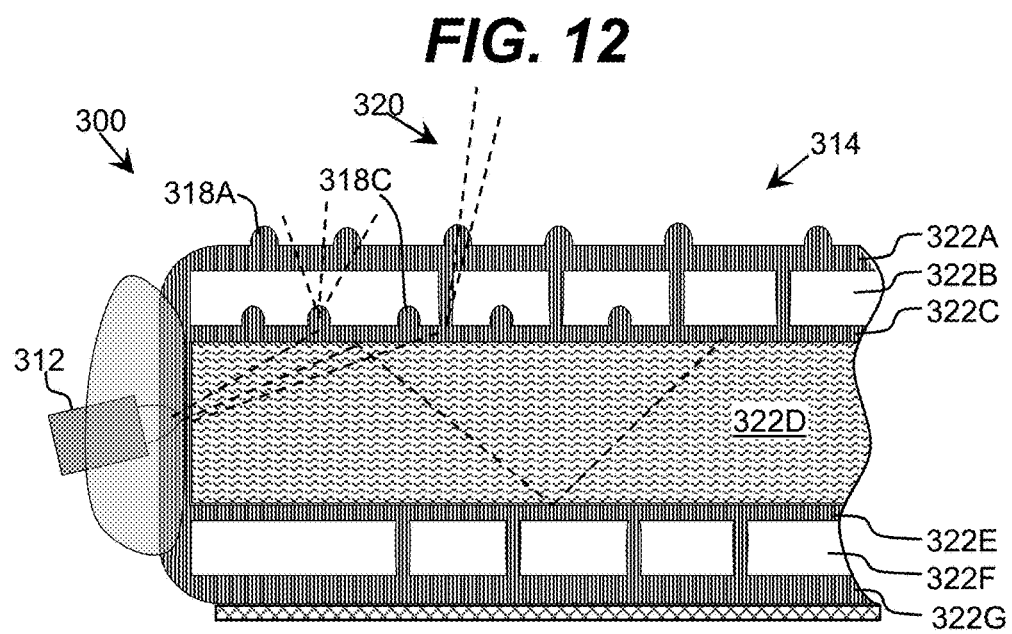
FIG. 12 shows an illustrative waveguide according to an embodiment.

FIG. 12 shows an illustrative wave guiding structure 300 according to an embodiment. The wave guiding structure 300 is coupled to an ultraviolet radiation source 312 and includes multiple layers 322A-322G. Some of the layers (e.g., layers 322A, 322C, 322E, 322G) each formed of a transparent material and sufficiently thin to provide a desired level of transparency, while other layers (e.g., layers 322B, 322D, 322F) are filled with a transparent fluid. The wave guiding structure 300 also includes an emission surface 314 through which diffused light 320 exits. The wave guiding structure 300 can further include diffusive elements 318A, 318C associated with at least one of the plurality of layers. Each diffusive element 318A, 318C can diffuse the light 320 to within forty percent of Lambertian distribution. The diffusive elements 318A, 318C can be arranged based on a desired uniformity of the diffused light 320 at a target distance corresponding to a surface to be illuminated. Aspects of this embodiment are related to U.S. patent application Ser. No. 14/853,0175, filed on 14 Sep. 2015 and U.S. Pat. No. 9,550,004, filed on 5 Sep. 2014, both of which are incorporated by reference.

Figure 13:
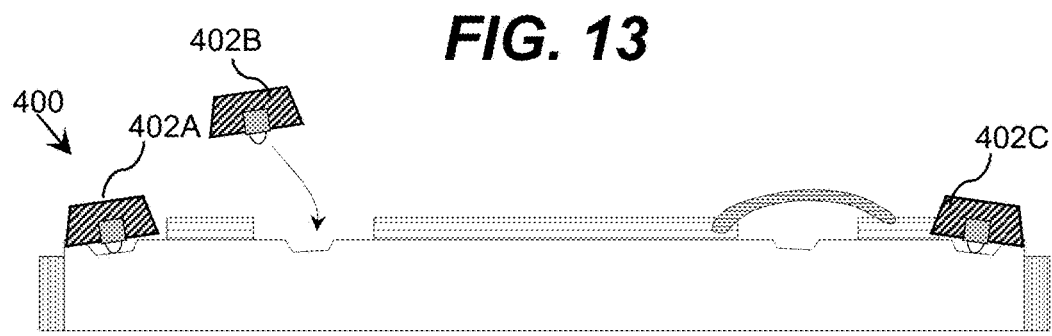
FIG. 13 shows an illustrative waveguide according to an embodiment.

FIG. 13 shows an illustrative wave guiding layer 400 according to an embodiment. Aspects of the wave guiding layer 400 are related to U.S. patent application Ser. No. 15/472,198, filed on 28 Mar. 2017, which is incorporated by reference. The wave guiding layer 400 includes a set of pluggable ultraviolet radiation sources 402A-402C. The pluggable ultraviolet radiation sources 402A-402C can provide a convenient embodiment for replacing the ultraviolet radiation sources 402A-402C if they have failed. In an embodiment, a socket can be developed to plug in different ultraviolet radiation sources 402A-402C depending on the target application. For instance, the ultraviolet radiation sources of different wavelength and intensity can be allowed to be plugged into a socket with the control power system capable of delivering sufficient current for operation of such ultraviolet radiation devices.

Figure 14:
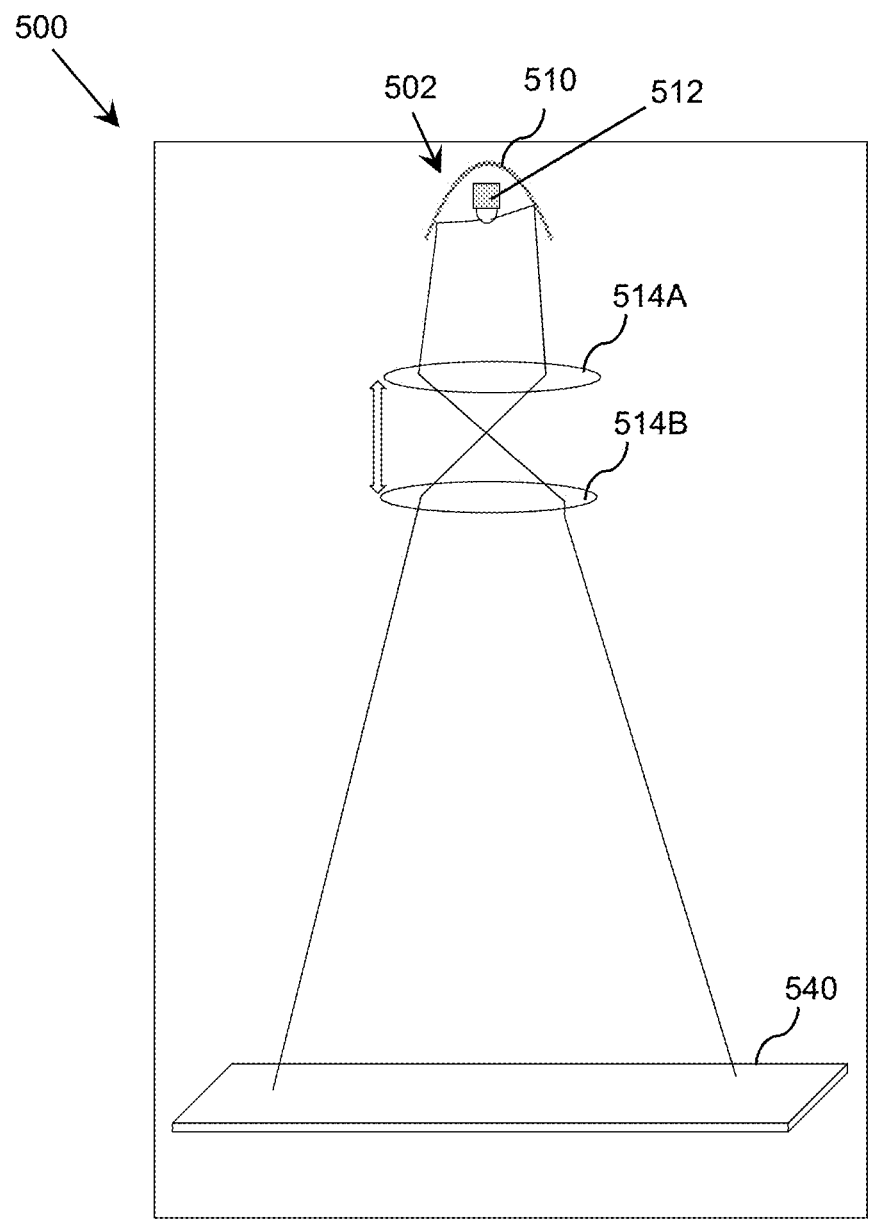
FIG. 14 shows an illustrative system according to an embodiment.

FIG. 14 shows an illustrative system 500 according to an embodiment. In this embodiment, the system 500 is in a vertical arrangement with respect to a target surface 540. The system 500 includes an illuminator 502 (e.g., a parabolic body 510 and a set of ultraviolet radiation sources 512 located in the proximity of a focus point of the parabolic body 510). The system 500 can also include a set of lenses 514A, 514B located between the set of ultraviolet radiation sources 512 and the target surface 540. Similar to the illuminator shown in FIG. 7, the position of the set of lenses 514A, 514B can be adjusted in order to change the ultraviolet radiation directed onto the target surface 540. In an embodiment, the set of lenses 514A, 514B are circular lenses and the target surface 540 is a circular surface. It is understood that the second lens 514B is not necessary in this embodiment.

Figure 15:
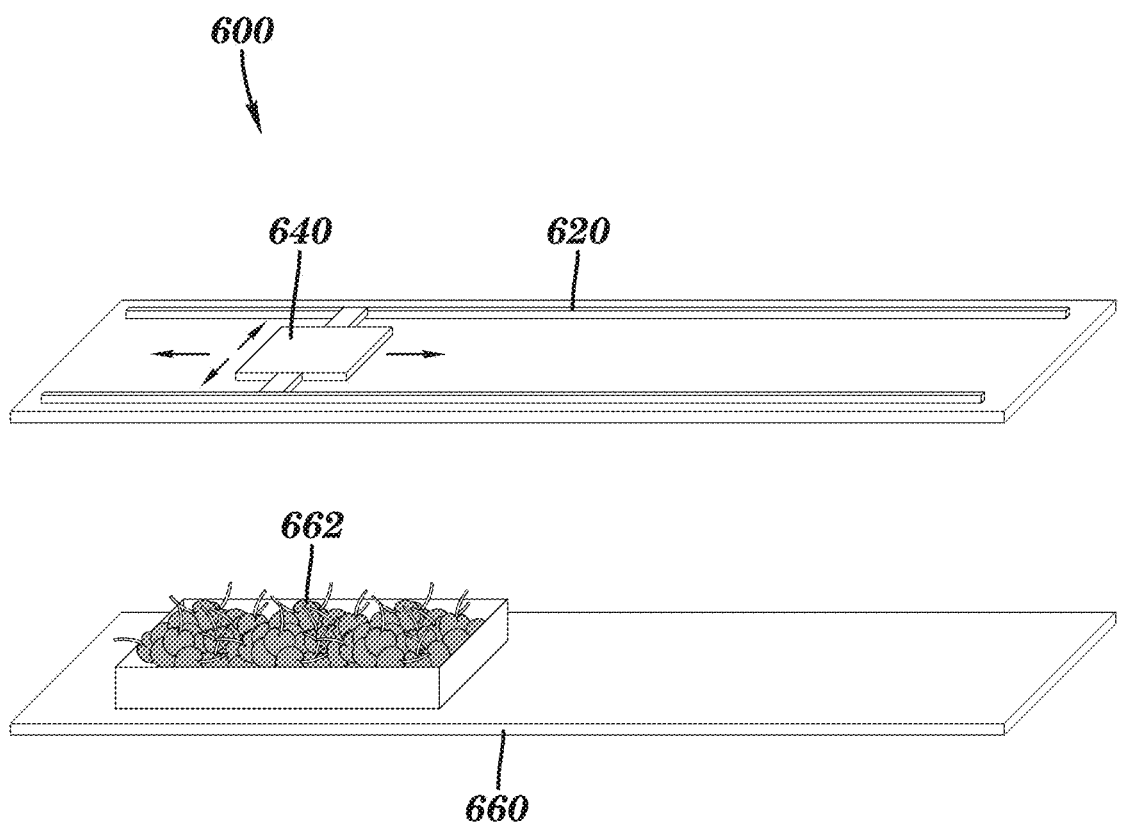
FIG. 15 shows an illustrative system according to an embodiment.

FIG. 15 shows an illustrative system 600 including an illuminator 640 according to an embodiment. The illuminator 640 can be any illuminator described herein. That is, the illuminator 640 can include any number of sources, lenses, mirrors, reflective surfaces, and/or the like, as discussed herein. In an embodiment, the illuminator 640 can include a lens formed of a fluoropolymer. In another embodiment, the illuminator 640 can include a Fresnel lens. The illuminator 640 is attached to a rail system 620 that allows the illuminator 640 to move in any direction. The system 600 includes a shelf 660 including a plurality of items 662. By allowing the illuminator 640 to move in any direction over the shelf 660, the illuminator 640 can target specific areas and/or items 662 within the shelf 660.

Figure 16:
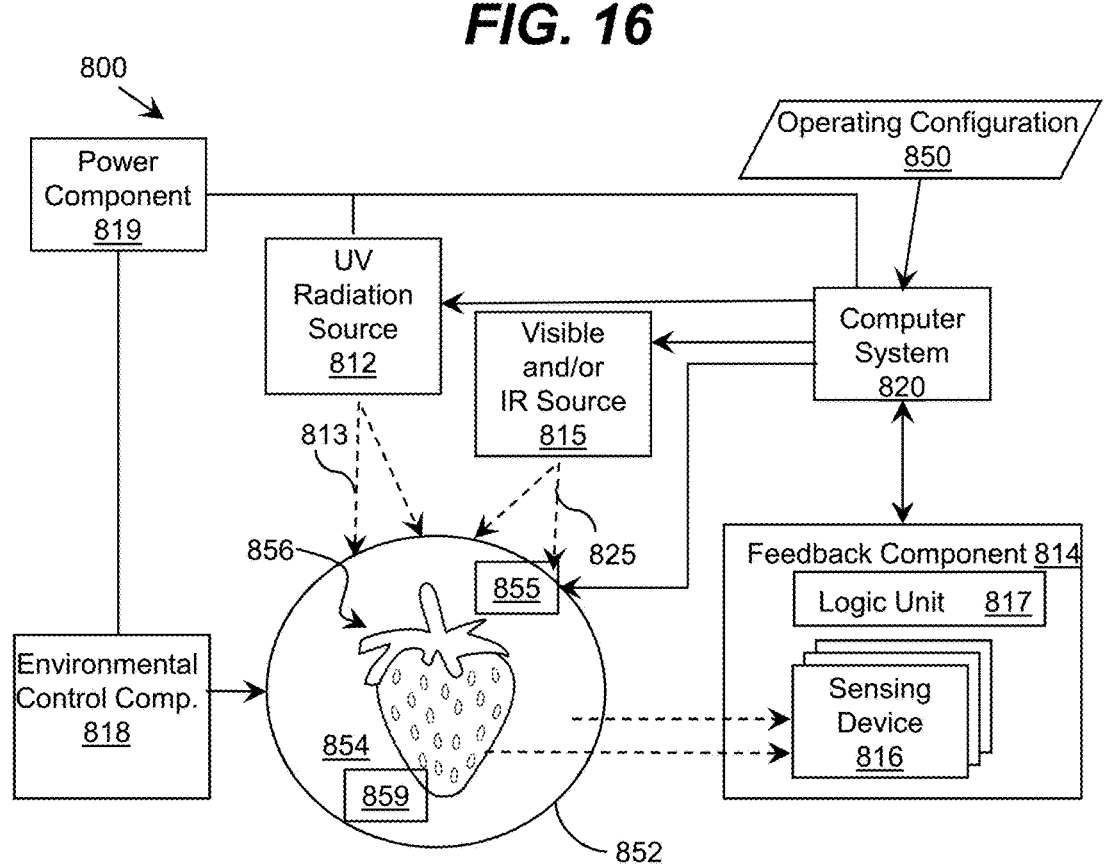
FIG. 16 shows an illustrative system according to an embodiment.

FIG. 16 shows an illustrative system including an ultraviolet radiation system 800 according to an embodiment. The computer system 820 is configured to control the ultraviolet radiation source 812 to direct ultraviolet radiation 813 into a storage area 854 of a storage device 852, within which a set of items 856 are located. The ultraviolet radiation source 812 can include aspects of an illuminator described herein (e.g., the illuminator 40 in FIG. 3A). The feedback component 814 is configured to acquire data used to monitor a set of current conditions of the storage area 854 and/or the items 856 over a period of time. As illustrated, the feedback component 814 can include a plurality of sensing devices 816, each of which can acquire data used by the computer system 820 to monitor the set of current conditions.

The feedback component 814 is configured to provide the data to a computer system 820 in order to adjust attributes of the ultraviolet radiation 813 based on the storage area 854 and/or the items 856 within the storage area 854. The feedback component 814 uses visual cameras, chemical sensors, mechanical sensors, infrared (IR) sensors, visible sensors, and/or UV sensors for detecting changes within the storage area 854 and/or the set of items 856. In an embodiment, the logic unit 817 receives data from a set of sensing devices 816 and provides data corresponding to the set of conditions of the storage area 854 and/or items 856 located in the storage area 854 for processing by the computer system 820. In a more particular embodiment, the computer system 820 can provide information corresponding to the currently selected operating configuration 850 for use by the feedback component 814. For example, the logic unit 817 can adjust the operation of one or more of the sensing devices 816, operate a unique subset of the sensing devices 816, and/or the like, according to the currently selected operating configuration 850. In response to data received from the feedback component 814, the computer system 820 can automatically adjust and control one or more aspects of the ultraviolet radiation 813 generated by the ultraviolet radiation source 812 according to the currently selected operating configuration 850. The aspects of the ultraviolet radiation 813 include a direction, an intensity, a pattern, a spectral power, a duration, and/or the like.

The plurality of operating configurations 850 can include a disinfection operating configuration, a storage life preservation operating configuration, and an ethylene decomposition operating configuration. Each operating configuration 50 includes a unique combination of: a target intensity, a target peak wavelength, and a target pattern for the ultraviolet radiation. The storage life preservation operating configuration can require an ultraviolet wavelength that is between approximately 285 nm to approximately 305 nm. In an embodiment, the target wavelength the storage life preservation operating configuration is approximately 290 nm peak emission of a relatively lower intensity substantially continuous radiation. For example, an illustrative intensity range can be between approximately 0.1 milliwatt/m$^2$ and approximately 1000 milliwatt/m$^2$. In an embodiment, the intensity for the ultraviolet radiation in the storage life preservation operating configuration can be approximately 400 microwatts/cm$^2$. In a more specific illustrative embodiment, the ultraviolet LEDs can direct ultraviolet radiation having an intensity of a few (e.g., 1-3) microwatts/cm$^2$ for approximately seven days within an enclosure that does not allow ultraviolet radiation to escape, such as an aluminum tube.

The disinfection operating configuration can require any subset of ultraviolet wavelengths in the range of ultraviolet wavelengths (e.g., between approximately 10 nm and approximately 400 nm) and higher intensity levels. In an embodiment, the intensity range can be between approximately 1 milliwatt/m$^2$ and approximately 10 watt/m$^2$. In a more specific embodiment, the ultraviolet wavelength and intensity levels for the disinfection operating configuration can be between approximately 250 nm to approximately 290 nm and approximately 20 microwatt/cm$^2$ or higher, respectively, and the ultraviolet light can be applied for approximately 20 minutes. In this case, the dosage of ultraviolet radiation for the disinfection operating configuration can be approximately 24 milliJoule/cm$^2$. However, it is understood that this is only illustrative and a dosage can be at least 16 miliJoule/cm$^2$. The ethylene decomposition operating configuration an ultraviolet wavelength range of approximately 285 nm to approximately 305 nm. In an embodiment, the intensity range can be between approximately 1 milliwatt/m$^2$ and approximately 1000 watt/m$^2$.

Additional aspects of the feedback component are related to U.S. Pat. No. 9,034,271, filed 28 Aug. 2013, which is hereby incorporated by reference.

In any of the embodiments, it is understood that several ultraviolet radiation sources can be included in the same illuminator and a control system can independently operate each ultraviolet radiation source. In addition, the system can include any number of sensors, such as an ozone sensor that is configured to monitor ozone levels in the ambient, a humidity sensor that is configured to monitor the humidity levels in the ambient, a temperature sensor, a chemical sensor (e.g., CO$_2$ sensor) and/or the like. Furthermore, the system can control attributes of the ambient (e.g., using the environmental control component 818). For example, the system can include a storage container with an illuminator according to one of the embodiments discussed herein for disinfecting the storage container and the storage container can include means for incorporating chemicals (e.g., baking soda and/or the like) to control the odor within the storage container.

It is further understood that environmental factors such as ambient temperature, air pressure, presence of ethylene and other factors can affect operation of the system. In an embodiment, the system can be designed to prolong the preservation of produce at room temperature (e.g., temperatures of about 70 Fahrenheit), refrigerator temperature of about 32-40 Fahrenheit, or at temperatures in the range between 32-70 F. In all cases, the system can employ UV radiation at a broad range of approximately 250 nm to approximately 380 nm, with produce preservation radiation in the range of approximately 285 nm to approximately 300 nm, sterilization UVC radiation with a peak radiation of approximately 270 nm to approximately 280 nm, and UVA radiation for disinfection using a photo-catalyst (e.g., TiO$_2$). In addition, UV radiation at various wavelengths can be employed for deactivation of ethylene. Furthermore, the UV radiation and sensing by the sensing devices 816 can be employed for detecting ozone levels within the ambient.

Figure 17:
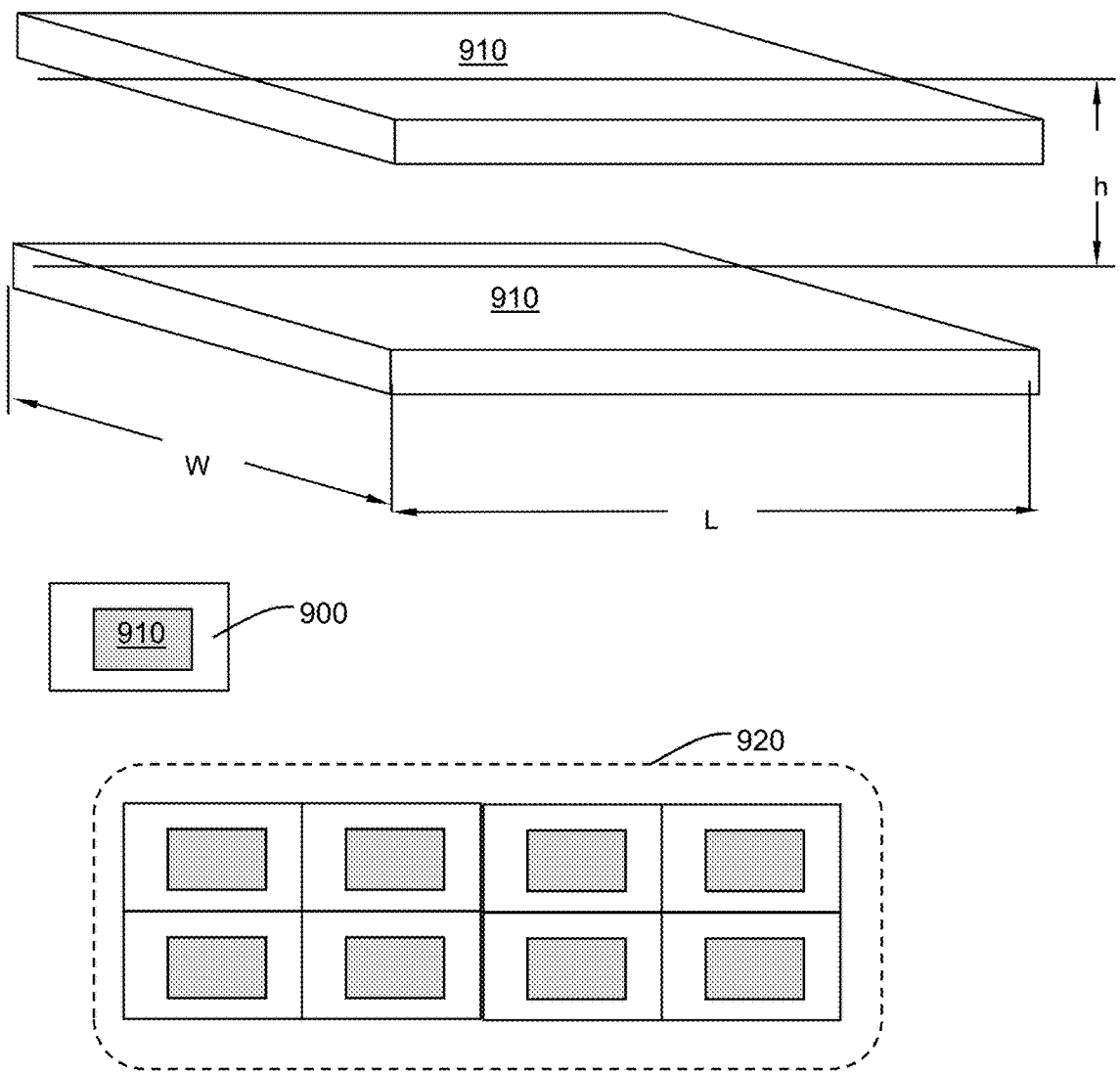
FIG. 17 shows an illustrative illuminator according to an embodiment.
Figure 18:
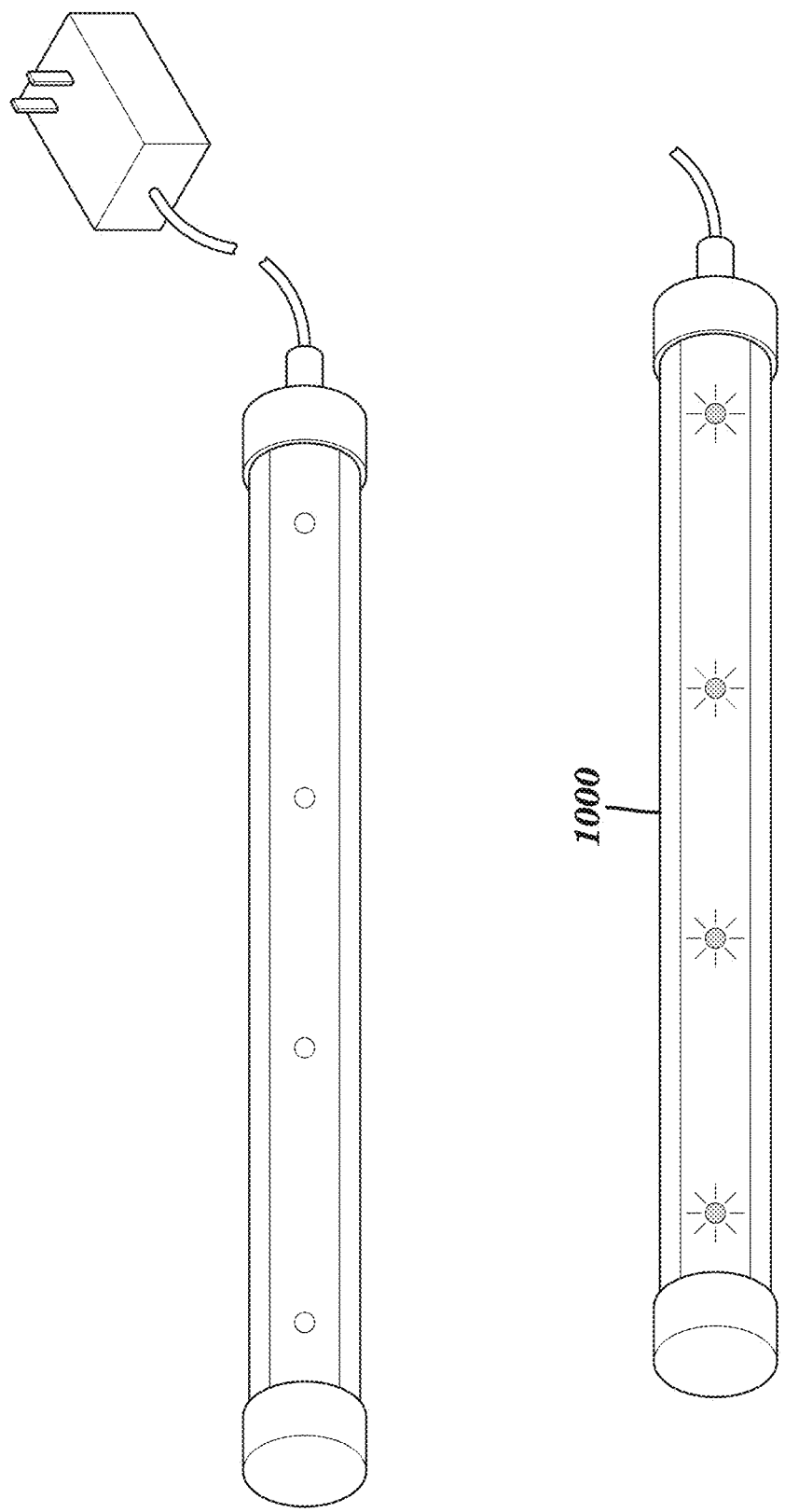
FIG. 18 shows an illustrative illuminator according to an embodiment.
Figure 19:
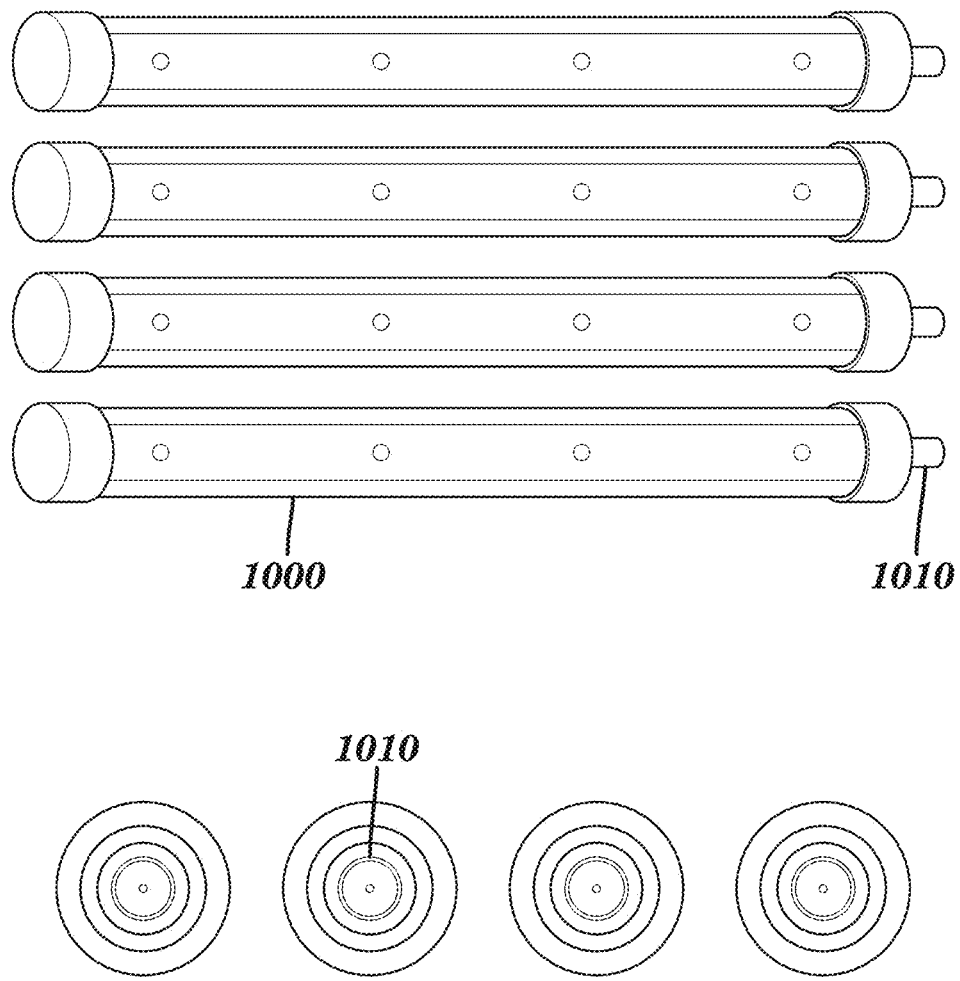
FIG. 19 shows illustrative electrical connections for an illuminator according to an embodiment.
Figure 20A:
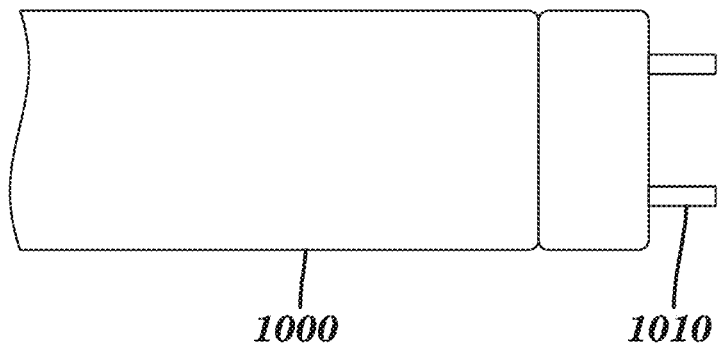
Figure 20B:
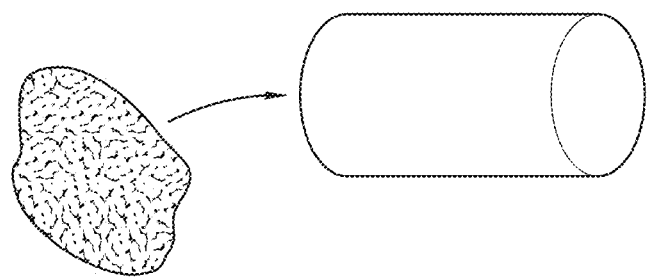
FIG. 20B shows an illustrative wave guide according to an embodiment.
Figure 21A:
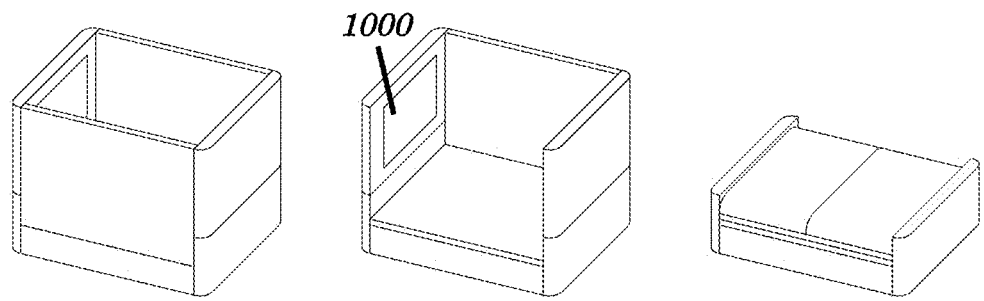
FIGS. 21A and 21B show portable devices that utilize illustrative illuminators according to embodiments.
Figure 21B:
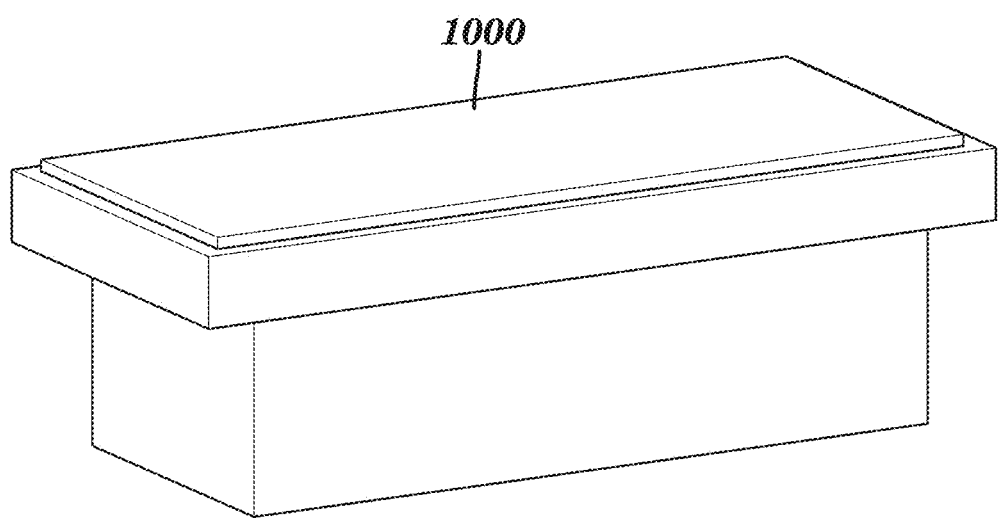

FIG. 17 shows an illustrative illuminator 900 according to an embodiment. The illuminator 900 can be configured to uniformly illuminate a rectangular area 910. In an embodiment, each illuminator 900 is designed to illuminate an area of $A_o=W_o*L_o$, where $W_o$ is the width and $L_o$ is the length of the illuminator 900. For an arbitrary area A, the number of illuminators is calculated by evaluating $N=A/A_0$. Alternatively, if the shelf is of the size $W_1*L_1$ then the number of illuminators can be estimated by: $W_1/W_0*L_1/L_0$. The rectangular region 910 that can be adequately irradiated by illuminator 900. The shelf 920 can be subdivided by a number of such areas 900 for thorough irradiation. It is understood that the embodiments of the illuminator described herein can be similar to a fluorescent tube. FIG. 18 shows an illustrative illuminator 1000 that is configured to look similar to a fluorescent tube. FIG. 19 shows illustrative electrical connections 1010 for an illuminator 1000. Therefore, the illuminator 1000 can be interchangeable with fluorescent tubes with similar connections 1010. FIG. 20A shows an illustrative illuminator 1000 designed to have connections similar to that of a fluorescent tube that has connections 1010 (e.g., T2, T4, T5, T8, T9, T10, T12, T17, PG17). For example, the connection 1010 is a T8 connection. In an embodiment, the exterior of the illuminator 1000 is a diffusive UV transparent fluoropolymer. In FIG. 20B, an illustrative illuminator 1000 according to an embodiment is shown. The illuminator 1000 can include waveguide elements and a transparent diffusive powder-like material on an exterior surface. FIGS. 21A and 21B show a plurality of portable containers, each of which can include one or more illuminators 1000 as discussed herein. For example, FIG. 21A shows stackable crates that can include at least one illuminator 1000, while FIG. 21B shows a storage container with at least one illuminator 1000.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
   an illuminator including:
     a reflective mirror; and
     a set of ultraviolet radiation sources located within a proximity of a focus point of the reflective mirror, the set of ultraviolet radiation sources configured to generate ultraviolet radiation directed at the reflective mirror, wherein the set of ultraviolet radiation sources are coupled by a diffusive waveguide structure;

a reflective surface located adjacent to the illuminator; and a set of optical elements located between the illuminator and the reflective surface, the set of optical elements configured to direct an ultraviolet radiation beam towards at least 50% of the reflective surface, wherein the reflective surface diffusively reflects at least 30% of the ultraviolet radiation.

2. The system of claim 1, wherein the reflective mirror is a parabolic reflector.

3. The system of claim 1, wherein the set of optical elements includes a first lens and a second lens.

4. The system of claim 3, wherein at least a portion of each lens includes a Fresnel lens.

5. The system of claim 3, wherein the second lens is movable with respect to the first lens.

6. The system of claim 1, further comprising at least one sensor coupled to the diffusive waveguide structure.

7. The system of claim 1, wherein the diffusive waveguide structure includes a plurality of roughness elements on a surface.

8. The system of claim 1, wherein the diffusive ultraviolet radiation is directed towards a target surface and the diffusive ultraviolet radiation is uniform over at least 20% of the target surface.

9. The system of claim 1, wherein the set of optical elements includes a total internal reflection lens.

10. The system of claim 1, further comprising a mesh located between the reflective surface and a target surface, wherein the mesh includes a photo-catalyst film.

11. The system of claim 1, further comprising a rail system, wherein the rail system is configured to move the illuminator with respect to a target surface.

12. A system comprising:
an illuminator including:
a reflective mirror; and
a set of ultraviolet radiation sources located within a proximity of a focus point of the reflective mirror, the set of ultraviolet radiation sources configured to generate ultraviolet radiation directed at the reflective mirror, wherein the set of ultraviolet radiation sources are coupled by a diffusive waveguide structure;

a reflective surface located adjacent to the illuminator; and a set of optical elements located between the illuminator and the reflective surface, the set of optical elements configured to direct an ultraviolet radiation beam towards at least 50% of the reflective surface, wherein the reflective surface diffusively reflects the ultraviolet radiation to within 40% of Lambertian distribution.

13. The system of claim 12, wherein the set of optical elements includes a first lens and a second lens.

14. The system of claim 13, wherein at least a portion of each lens includes a Fresnel lens.

15. The system of claim 13, wherein the second lens is movable with respect to the first lens.

16. The system of claim 12, wherein the diffusive waveguide structure includes a plurality of roughness elements on a surface.

17. The system of claim 12, wherein the diffusive ultraviolet radiation is directed towards a target surface and the diffusive ultraviolet radiation is uniform over at least 20% of the target surface.

18. The system of claim 12, wherein the set of optical elements includes a total internal reflection lens.

19. A system comprising:
a set of illuminators, each illuminator including:
a reflective mirror; and
a set of ultraviolet radiation sources located within a proximity of a focus point of the reflective mirror, the set of ultraviolet radiation sources configured to generate ultraviolet radiation directed towards the reflective mirror, wherein the set of ultraviolet radiation sources are coupled by a diffusive waveguide structure;

a reflective surface located between the set of illuminators; and a set of optical elements located between each illuminator and the reflective surface, the set of optical elements configured to direct an ultraviolet radiation beam towards at least 50% of the reflective surface, wherein the reflective surface diffusively reflects the ultraviolet radiation to within 40% of Lambertian distribution.

20. The system of claim 19, wherein the set of optical elements includes a set of lenses.

* * * * *